United States Patent
Gerber et al.

(10) Patent No.: US 11,957,792 B2
(45) Date of Patent: Apr. 16, 2024

(54) TASTE-MASKED PHARMACEUTICAL COMPOSITIONS CONTAINING DICLOFENAC

(71) Applicant: GLATT AG, Pratteln (CH)

(72) Inventors: Frédéric Gerber, Blotzheim (FR); Marie Guhmann, Huningue (FR); Norbert Pöllinger, Müllheim (DE)

(73) Assignee: Glatt AG, Pratteln (CH)

( * ) Notice: Subject to any disclaimer, the term of this patent is extended or adjusted under 35 U.S.C. 154(b) by 0 days.

(21) Appl. No.: 14/240,008

(22) PCT Filed: Apr. 19, 2013

(86) PCT No.: PCT/EP2013/001173
§ 371 (c)(1),
(2) Date: Feb. 20, 2014

(87) PCT Pub. No.: WO2013/156163
PCT Pub. Date: Oct. 24, 2013

(65) Prior Publication Data
US 2014/0193497 A1    Jul. 10, 2014

(30) Foreign Application Priority Data
Apr. 19, 2012   (EP) .................................... 12002749

(51) Int. Cl.
| | |
|---|---|
| *A61K 9/20* | (2006.01) |
| *A61K 9/00* | (2006.01) |
| *A61K 9/16* | (2006.01) |
| *A61K 9/50* | (2006.01) |
| *A61K 31/196* | (2006.01) |

(52) U.S. Cl.
CPC .......... *A61K 9/2027* (2013.01); *A61K 9/0056* (2013.01); *A61K 9/1623* (2013.01); *A61K 9/1635* (2013.01); *A61K 9/1652* (2013.01); *A61K 9/2077* (2013.01); *A61K 9/2081* (2013.01); *A61K 9/5026* (2013.01); *A61K 9/5073* (2013.01); *A61K 9/5078* (2013.01); *A61K 31/196* (2013.01)

(58) Field of Classification Search
None
See application file for complete search history.

(56) References Cited

U.S. PATENT DOCUMENTS

| | | | |
|---|---|---|---|
| 6,153,220 A | * | 11/2000 | Cumming ............ A61K 9/1635 424/441 |
| 6,197,348 B1 | | 3/2001 | Morella et al. |
| 2006/0039981 A1 | | 2/2006 | Murpani et al. |
| 2008/0069878 A1 | * | 3/2008 | Venkatesh ............ A61K 9/5026 424/468 |
| 2009/0291137 A1 | | 11/2009 | Guimberteau et al. |

FOREIGN PATENT DOCUMENTS

| | | | |
|---|---|---|---|
| EP | 0 052 075 | 5/1982 | |
| EP | 0 350 701 | 1/1990 | |
| EP | 0 365 480 | 4/1990 | |
| EP | 0 599 767 | 6/1994 | |
| GB | 2 217 598 | 11/1989 | |
| WO | WO 97/44023 | 11/1997 | |
| WO | WO-2005115352 A1 * | 12/2005 | ........... A61K 9/2866 |
| WO | WO2009086338 | * 7/2009 | |

OTHER PUBLICATIONS http://www.matweb.com/search/datasheettext.aspx?matguid=139289bd54194ebaa4e8539ac4fe4a8c (Year: 2021).*
International Search Report for PCT/EP2013/001173 dated May 31, 2013.
Zelalem Ayenew et al., *Trends in Pharmaceutical Taste Masking Technologies: A Patent Review*, 2009 Bentham Science Publishers Ltd., Recent Patents on Drug Delivery & Formulation, 2009, vol. 3, 26-39.

* cited by examiner

*Primary Examiner* — David J Blanchard
*Assistant Examiner* — Sarah J Chickos
(74) *Attorney, Agent, or Firm* — Eugene LeDonne; Jon E. Gordon; Haug Partners LLP

(57) ABSTRACT

A pharmaceutical composition is described which includes diclofenac as an active ingredient. The pharmaceutical composition further includes a (meth)acrylic polymer which has a specific solubility and/or a particular functional group in one polymer component.

9 Claims, 10 Drawing Sheets

//TASTE-MASKED PHARMACEUTICAL COMPOSITIONS CONTAINING DICLOFENAC

The present application claims priority from PCT/EP2013/001173 filed on Apr. 19, 2013, which claims priority from European Patent Application No. EP 12002749.5 filed on Apr. 19, 2012, the disclosures of which are incorporated herein by reference in their entirety.

1. FIELD OF THE INVENTION

The present invention is directed to taste-masked pharmaceutical compositions containing diclofenac. The name of the active ingredient in the pharmaceutical compositions of the invention, i.e. "diclofenac", is the International Non-Proprietary Name (INN) of the chemical compound 2-[(2,6-Dichlorophenyl)amino]benzeneacetic acid. Diclofenac is especially used in the treatment of pain, of inflammatory disorders, and of dysmenorrhoea.

It is noted that citation or identification of any document in this application is not an admission that such document is available as prior art to the present invention.

The compound diclofenac is typically administered via the oral route. Diclofenac or a pharmaceutical composition containing diclofenac which is orally administered is exposed to different media with different pH values, i.e. the oral cavity (saliva with pH 6.2-7.4), the stomach (gastric fluid with pH 1.1-1.6) and finally the intestine (intestinal fluid with pH~6.8), the site of absorption of diclofenac.

Diclofenac itself is a poorly soluble and highly permeable weak acid. Its bioavailability from solid oral dosage forms is mostly controlled by the rate and extent of disintegration of the solid dosage form in the gastrointestinal tract prior to the dissolution of diclofenac in the intestine. Therefore, absorption of diclofenac is more rapidly effective if it is administered in dispersed or dissolved form, such as suspension, powder or granules dispersed in water. However, diclofenac has a bitter taste so that oral formulations may be very unpleasant for the treated individual, thereby negatively influencing the patient compliance. It was shown in previous literature work that even the free acid of diclofenac, much less soluble than sodium and potassium salts, shows bitter aftertaste properties and thus, compromise the palatability of a pharmaceutical dosage form.

Accordingly, various attempts have been made in order to provide diclofenac-containing formulations with delayed or immediate release characteristics which have an acceptable taste.

In WO 97/44023 A1, palatable pharmaceutical compositions of diclofenac with immediate release characteristics are described which contain alkali metal carbonates, bicarbonates and flavouring substances. Some examples include a granulation step in which diclofenac and further excipients are wet-granulated. WO 97/44023 A1 further discloses that due to its poor solubility in water, diclofenac is normally used in salt form.

EP 0 365 480 A1 refers to dispersible solid drug formulations comprising finely divided diclofenac and a certain amount of disintegrant, wherein the diclofenac is in the free acid form having a particle size diameter of from about 4 to about 100 μm. The constituents of the described drug formulations are typically granulated, and the granulate is thereafter compressed into tablets, which disintegrate quickly when dropped into water.

Further, EP 0 052 075 A1 discloses granular drug retard forms containing a granulated or crystalline active ingredient and a retarding shell, which shell basically consists of a mixture of a polyacrylic acid ester and a cellulose ether both of which are not soluble in water but are dispersible in water. In an example, a core containing sodium diclofenac is provided with a shell which encompasses the (meth)acrylic component Eudragit® NE 30 D, formerly named Eudragit E 30 D. According to its product characteristics, this polymeric component is insoluble, has a low permeability and a pH independent swelling. However, the pharmaceutical compositions of EP 0 052 075 A1 are drug retard forms and therefore, diclofenac is delayed-released.

Taste-masked pharmaceutical compositions are also reported in U.S. Pat. No. 6,197,348 B1. In one example, taste-masked diclofenac is produced by spray drying, in which a coating is employed which contains a polymer with quaternary ammonium groups on the polymer backbone, namely Eudragit® RS-100. Like Eudragit® NE 30 D, the polymeric component Eudragit® RS-100 is said in its product characteristics to be insoluble, to have a low permeability and to have a pH-independent swelling. Therefore, the taste-masked pharmaceutical compositions of U.S. Pat. No. 6,197,348 B1 are not suitable for immediate release of the active compound, since they are sustained-released formulations.

In EP 0 350 701 A2, pharmaceutical compositions are described which shall have an analgesic and anti-inflammatory activity, and which comprise an active ingredient selected from a list of various active ingredients, diclofenac being one member of the list. The disclosed compositions further include substances protecting the mucous membranes which also have taste-masking properties. The protective substances can be of various chemical nature and can e.g. be gastro-soluble or gastro-resistant substances. Acrylic and methacrylic acid derivatives are generally mentioned in this context in lists (Eudragit® classes E, S and L), but not further specified. In addition, the release characteristics of the pharmaceutical compositions of EP 0 350 701 A2 are not addressed.

Document EP 0 599 767 A1 refers to a process to prepare water-dispersible tablets containing diclofenac. Such tablets are made from granules which comprise micronized diclofenac with a particle size of less than 10 μm, a hydrophilic lubricant and a disintegrant. Typically, a flavour and a sweetener are added to provide adequate organoleptic characteristics.

Diclofenac formulations with an improved taste are further reported in GB 2 217 598 A, wherein finely particulate diclofenac is provided with a permeable, swellable coating. Polyacrylates may be used as a coating material, and in examples describing effervescent tablets, the polymer Eudragit® NE 30 D (formerly named Eudragit® E 30 D) is used. This polymer is insoluble and is known to have a low permeability and a pH-independent swelling.

In US patent application 2009/0291137 A1, solid forms intended for oral administration and capable of guaranteeing a double release mechanism of a contained active ingredient are described. In one example, the active ingredient is sodium diclofenac which is granulated with further excipients. The granules are coated with a mixture of Eudragit® L 100-55, Eudragit® RS100 and triethylcitrate. As mentioned above, Eudragit® RS-100 is insoluble, has a low permeability and further has a pH-independent swelling, whereas Eudragit® L 100-55 contains an anionic copolymer and dissolves above pH 5.5. According to its product characteristics, Eudragit® L 100-55 provides effective and stable enteric coatings and are used to obtain a delayed-release.

Another US patent application 2006/0039981 A1 discloses taste-masked dosage forms comprising diclofenac sodium and one or more cationic polymers, such as for example, EUDRAGIT E-100 or EUDRAGIT E PO, wherein the weight ratio of the drug to polymer is less than one to two.

U.S. Pat. No. 6,153,220 provides a taste-masked pharmaceutical powder comprising micromatrices containing diclofenac sodium and EUDRAGIT E, wherein the wt/wt ratio of the copolymer to the drug is greater than 2 to 1 and wherein the micromatrices have an average size from about 1 μm to 125 μm, preferably 1 μm to 30 μm. Furthermore, it is disclosed that the powder is formed by spray-drying a solution or dispersion containing the drug and copolymer.

Some oral diclofenac compositions with suitable taste-masking properties tend to exhibit inferior release profiles of the active ingredient, i.e. of diclofenac. On the other hand, where oral diclofenac compositions have very suitable release profiles, there is a tendency for insufficient taste-masking properties and consequently insufficient patient compliance characteristics. In particular, there are several diclofenac-containing compositions provided in the prior art, which all are somehow taste-masked. However, none of the prior art describes a pharmaceutical composition easily to be swallowed, having a sufficient taste-masking and at the same time which allows diclofenac to be rapidly absorbed in the intestine. Such rapid absorption of diclofenac, however, is essential in order to provide a more quick therapeutic effect, in particular, when the treatment of pain is concerned.

It would therefore be desirable to have a diclofenac-containing pharmaceutical composition which has sufficient and possibly improved patient compliance characteristics, and which at the same time secures and improves the release characteristics of the contained diclofenac so as to safeguard the intended pharmaceutical effect. In particular, there is a need for a pharmaceutical composition containing diclofenac, which is virtually tasteless at the site of administration, i.e. in the mouth, and which at the same time ensures fast disintegration of the pharmaceutical composition prior to a fast dissolution of diclofenac at the site of absorption, i.e. in the intestine, in order to allow a fast onset of the therapeutic effects.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

Accordingly, it is an object of the present invention to provide an improved pharmaceutical composition of diclofenac. It is a particular object of the present invention to provide a pharmaceutical composition of diclofenac with advantageous patient compliance characteristics, whilst simultaneously ensuring suitable drug release profiles. More precisely, it is an object of the invention to provide a pharmaceutical composition of diclofenac exhibiting sufficient taste-masking properties and at the same time being rapidly effective due to improved release characteristics, i.e. improved disintegration characteristics of the pharmaceutical composition and dissolution characteristics of diclofenac. It is another object of the present invention to provide readily administrable oral forms of such improved pharmaceutical compositions of diclofenac.

In view of the above objects, the present invention provides a pharmaceutical composition comprising diclofenac or a pharmaceutically acceptable salt thereof as an active ingredient and a (meth)acrylic polymer which is soluble in an aqueous medium at a pH value of ≤5.0.

As stated above, "diclofenac", is the International Non-Proprietary Name (INN) of the chemical compound 2-[(2, 6-Dichlorophenyl)amino]benzeneacetic acid. Therefore, in the context of the present invention the term "diclofenac" refers to diclofenac in the free acid form.

A (meth)acrylic polymer which is soluble in an aqueous medium at a pH value of ≤5.0 is stable in the mouth (saliva a with range of about pH 62-7.4), i.e. the pharmaceutical composition of the present invention will not disintegrate during swallowing ensuring sufficient taste-masking properties (FIG. 16).

A (meth)acrylic polymer according to the invention is a polymer with at least one polymeric component derivable from the group of monomers selected from the group consisting of acrylic acid, an acrylic acid derivative, (meth)acrylic acid, or a (meth)acrylic acid derivative. Preferably, the (meth)acrylic polymer according to the invention consists of one or more polymeric components derivable from the group of monomers selected from the group consisting of acrylic acid, an acrylic acid derivative, (meth)acrylic acid, and/or a (meth)acrylic acid derivative.

Said polymeric component is to be understood as part of the polymeric structure which is receivable by polymerization of the corresponding type of monomers, optionally with further types of monomers. However, the definition of the (meth)acrylic polymer according to the invention is not limited as regards the way of producing it. This is clarified by the term "derivable" as used above.

A suitable acrylic or methacrylic acid derivative is the reaction product with an alcohol, i.e. the respective acrylic or methacrylic ester. Preferred esters are those derived from aliphatic alcohols, optionally substituted with functional groups like an amino group. More preferably, said esters are those derived from acyclic aliphatic alcohols, optionally substituted with functional groups like an amino group. Still more preferably, said esters are those derived from acyclic alkanols, optionally substituted with functional groups like an amino group. The amount of carbon atoms of said alcohols is preferably within the range of 1 to 4, not considering the carbon atoms of optional functional groups like an amino group.

The solubility at a pH value of 5.0 is one under standard ambient temperature and pressure (25° C., 100 kPa). It can be expressed in descriptive terms (see e.g. Remington's Pharmaceutical Sciences, 18th Edition, 1990, Chapter 16, page 208), which terms are as follows:

| Descriptive Terms | Parts of Solvent for 1 Part of Solute |
|---|---|
| Very soluble | Less than 1 |
| Freely soluble | From 1 to 10 |
| Soluble | From 10 to 30 |
| Sparingly soluble | From 30 to 100 |
| Slightly soluble | From 100 to 1000 |
| Very slightly soluble | From 1000 to 10,000 |
| Practically insoluble, or insoluble | More than 10,000 |

The (meth)acrylic polymer, which is soluble in an aqueous medium at a pH value of <5.0, satisfies the requirements for "Freely soluble" according to the above table.

The aqueous medium which is used for determining the solubility of the (meth)acrylic polymer is basically water, which has been acidified to the desired pH value by means of a suitable acid, e.g. hydrochloric acid or sulphuric acid. The diclofenac in such a pharmaceutical composition is taste-masked in a very suitable manner, and is at the same time released from the pharmaceutical composition in a way which ensures the pharmacologic effect in the treated patient.

With a pH value of ≤5.0, it is meant that the pH value of the aqueous medium is 5.0 or below 5.0. The same understanding applies analogously wherever the expression "≤" is used. Similarly, "≥" herein refers to equal to or larger than the indicated value.

The present invention further provides a pharmaceutical composition comprising diclofenac or a pharmaceutically acceptable salt thereof and a (meth)acrylic polymer having at least one amino group containing component.

An amino group as addressed in the present specification can be a primary amino group, a secondary amino group or a tertiary amino group, but not an ammonium group. A tertiary amino group is particularly advantageous for achieving improved taste-masking properties. Similar to what has been described for the pharmaceutical composition comprising a (meth)acrylic polymer with a particular solubility, the diclofenac in such a pharmaceutical composition with a (meth)acrylic polymer having at least one amino group containing component is likewise taste-masked in a very suitable manner, and is at the same time released such that the pharmacologic effect in the treated patient is achieved.

It is preferable that the above-mentioned (meth)acrylic polymer, which is soluble in an aqueous medium at a pH value of ≤5.0, also has at least one amino group containing component. A composition containing such a (meth)acrylic polymer jointly exhibits the effects described above for the two conceived (meth)acrylic polymers.

According to the invention, it is preferred that the above-mentioned (meth)acrylic polymer—i.e. the (meth)acrylic polymer which is soluble in an aqueous medium at a pH value of ≤5.0, the (meth)acrylic polymer having at least one amino group containing component, or the (meth)acrylic polymer which is soluble in an aqueous medium at a pH value of ≤5.0 and furthermore has at least one amino group containing component (which will herein referred to jointly as the "(meth)acrylic polymer", unless specifically stated otherwise)—is actually poly(butyl methacrylate-co-(2-dimethylaminoethyl)methacrylate-co-methyl methacrylate).

Whilst the (meth)acrylic polymer according to the invention may have only one polymer component, or may have two, three or even four and more polymer components, it has been found that a copolymer having three specific polymer components of those mentioned above is particularly useful for achieving the objects of the present invention. A pharmaceutical diclofenac composition comprising poly(butyl methacrylate-co-(2-dimethylaminoethyl)methacrylate-co-methyl methacrylate) in fact exhibits particularly suitable release profiles of diclofenac. The advantageous release profiles do however not come at the cost of bad taste. Instead, such a pharmaceutical diclofenac composition has very good taste-masking properties and leads to favourable patient compliance characteristics.

The amount of the (meth)acrylic polymer in general and the poly(butyl methacrylate-co-(2-dimethylaminoethyl) methacrylate-co-methyl methacrylate) in particular can vary. However, for cost-saving reasons on the one hand and a simple processing of the mentioned polymer in the manufacture of the pharmaceutical compositions of the invention on the other hand, it is preferable that the mentioned polymers are present in the pharmaceutical composition in an amount in the range of ≥0.1 to ≤50.0% by weight (or weight %, hereinafter abbreviated as wt. %), based on the total weight of the pharmaceutical composition. The total weight of the pharmaceutical composition is always the basis for relative amounts indicated in this specification, unless explicitly stated otherwise. The relative amount is more preferably in the range of ≥0.1 to ≤30.0 wt. %, still more preferably in the range of ≥1.0 to ≤20.0 wt. %.

A relative amount of the (meth)acrylic polymer of ≥1.0 to ≤20.0 wt. % allows to provide a pharmaceutical composition exhibiting sufficient taste-masking properties and at the same time fast release characteristics. Since the bioavailability of diclofenac from solid oral dosage forms is controlled by the rate and extent of disintegration of the solid dosage form, the amount of the (meth)acrylic polymer limiting disintegration is crucial for immediate-release characteristics. The amount of the (meth)acrylic polymer correlates to its ability to dissolve in the acidic medium, i.e. in the stomach. Hence, lesser amounts of the (meth)acrylic polymer results in a faster disintegration of the pharmaceutical composition of the present invention. Thereby, diclofenac is faster released from the pharmaceutical composition of the present invention. In summary, the amount of the (meth) acrylic polymer finally influences the release characteristics of the pharmaceutical compositions.

However, where the pharmaceutical composition is composed of either granules in which diclofenac and one of the mentioned polymers are co-present, in other words in which they are homogenously mixed, or of pellets with a diclofenac-containing core and a coating comprising the (meth)acrylic polymer, especially poly(butyl methacrylate-co-(2-dimethylaminoethyl)methacrylate-co-methyl methacrylate), particular relative amounts may apply. This is detailed further below.

Additional aspects of the (meth)acrylic polymer used in the invention also influence the characteristics of the pharmaceutical composition. More particularly, a comparably fast release of the active ingredient diclofenac and a good large-scale processability of the employed starting materials are achieved when materials and especially a (meth)acrylic polymer of low viscosity are employed. In case a later colouring of the final dosage forms is contemplated, the materials and again especially the (meth)acrylic polymer of the pharmaceutical composition should have a high pigment binding capacity. Where the (meth)acrylic polymer is part of a coating, it is further desirable that it has a good adhesion in order to secure a good adhesion of the coating on the coated substance. It has been found that the below aspects are favourable in order to realize such properties of the pharmaceutical composition and the comprised (meth) acrylic polymer, respectively.

Accordingly, in a first further aspect of the invention, in which the (meth)acrylic polymer is poly(butyl methacrylate-co-(2-dimethylaminoethyl)methacrylate-co-methyl methacrylate), it is preferred that the ratio of butyl methacrylate to (2-dimethylaminoethyl)methacrylate to methyl methacrylate is in the range of 0.5-2:1-3:1, more preferred in the range of 0.8-1.2:1.5-2.5:1, and especially preferred 1:2:1.

In a second further aspect of the invention, it is preferred that the (meth)acrylic polymer preferably has a weight average molar mass in the range of 40,000 to 54,000 g/mol, more preferred in the range of 44,000 to 50,000 g/mol, and especially preferred of 47,000 g/mol.

In a third further aspect of the invention, it is preferred that the (meth)acrylic polymer has an alkali value in the range of 160 to 200 KOH/g polymer, more preferred in the range of 170 to 190 KOH/g polymer, and especially preferred of 180 KOH/g polymer. The alkali value (or hydroxyl number) is a measure of the number of hydroxyl groups contained in the polymer. It indicates the weight in milligrams of KOH which is necessary to neutralize the hydroxyl groups in one gram of the tested polymer. The alkali value is determined by acetylation using acetic anhydride and by titration of the acetic acid and excess anhydride with potassium hydroxide.

In a fourth further aspect of the invention, it is preferred that the (meth)acrylic polymer has a glass transition temperature in the range of 40 to 56° C., more preferred in the range of 44 to 52° C., and especially preferred of 48° C. It can be determined by differential scanning calorimetry, see e.g. ISO 11357-2:1999.

When one or more of the above aspects are realized, the favourable characteristics of the pharmaceutical composition are realized. However, the more aspects are realized at the same time, the more prominent the advantageous effects are. It is therefore especially preferred that the first further aspect and the second further aspect, the first further aspect and the third further aspect, the first further aspect and the fourth further aspect, the second further aspect and the third further aspect, the second further aspect and the fourth further aspect, or the third further aspect and the fourth further aspect, are simultaneously fulfilled. It is more preferred that the first further aspect, the second further aspect and the third further aspect, the first further aspect, the second further aspect and the fourth further aspect, or the second further aspect, the third further aspect and the fourth further aspect, are simultaneously fulfilled. It is even more preferred that all four aspects, i.e. the first further aspect, the second further aspect, the third further aspect and the fourth further aspect, are simultaneously fulfilled.

It follows that in order to achieve the objectives of the present invention, it is particularly suitable that the (meth) acrylic polymer is poly(butyl methacrylate-co-(2-dimethylaminoethyl)methacrylate-co-methyl methacrylate), wherein
preferably, the ratio of butyl methacrylate to (2-dimethylaminoethyl)methacrylate to methyl methacrylate is in the range of 0.5-2:1-3:1, the (meth)acrylic polymer has a weight average molar mass in the range of 40,000 to 54,000 g/mol, the (meth)acrylic polymer has an alkali value in the range of 160 to 200 KOH/g polymer, and the (meth)acrylic polymer has a glass transition temperature in the range of 40 to 56° C.;
more preferably, the ratio of butyl methacrylate to (2-dimethylaminoethyl)methacrylate to methyl methacrylate is in the range of 0.8-1.2:1.5-2.5:1, the (meth) acrylic polymer has a weight average molar mass in the range of 44,000 to 50,000 g/mol, the (meth)acrylic polymer has an alkali value in the range of 170 to 190 KOH/g polymer, and the (meth)acrylic polymer has a glass transition temperature in the range of 44 to 51° C.; and
still more preferably, the ratio of butyl methacrylate to (2-dimethylaminoethyl)methacrylate to methyl methacrylate is 1:2:1, the (meth)acrylic polymer has a weight average molar mass of 47,000 g/mol, the (meth) acrylic polymer has an alkali value of 180 KOH/g polymer, and the (meth)acrylic polymer has a glass transition temperature of 47° C.

In view of the above-mentioned objects of the present invention, the pharmaceutical composition as herein described exhibits taste-masking properties in order to guarantee that a patient administering the pharmaceutical composition orally does not refrain from a persistent administration when necessary due to an unpleasant taste, so that a suitable patient compliance is achieved.

It is further conceivable that a pharmaceutical composition according to the present invention contains one or more additional active ingredients apart from diclofenac. However, where diclofenac is the only active ingredient in the pharmaceutical composition, the taste-masking properties are particularly advantageous. Further, the diclofenac can be present in free form or in salt form, i.e. in the form of a pharmaceutically acceptable salt. In the latter case, it is preferable that diclofenac is present as the sodium salt or the potassium salt.

Preferably, the pharmaceutical composition of the present invention comprises diclofenac in its free acid form. In this respect, it has been surprisingly found that after oral administration of a pharmaceutical composition of the present invention comprising diclofenac in the free acid form exhibits improved drug release characteristics in the intestine. In particular, it has been further found that after oral administration of a pharmaceutical composition of the present invention comprising diclofenac in the free acid form exhibits improved drug release characteristics in the intestine compared to a pharmaceutical composition of the present invention comprising diclofenac as a pharmaceutically salt, such as, diclofenac sodium or diclofenac potassium.

After oral administration the pharmaceutical composition of the present invention is first exposed to the mouth (saliva, pH range of about 6-7.4), passes the stomach (gastric fluid of acidic pH of about 1.1-1.6) and finally ends up in the small intestine (intestinal fluid of pH of about 6.8), where diclofenac is absorbed.

It is known that diclofenac in the free acid form is less soluble than diclofenac sodium or diclofenac potassium in most of the media and pH conditions. The poor solubility of diclofenac acid is, for instance, also described in WO 97/44023 A1 stating that due to its poor solubility in water, diclofenac is normally used in salt form. The poorer solubility of diclofenac acid could result in lesser ability to dissolve at the site of absorption, i.e. the intestine, than the salts. Therefore, diclofenac is normally used in salt form in cases where dissolved diclofenac is desired in order to ensure a rapid absorption and thereby a rapid onset of the therapeutic effect of diclofenac.

Surprisingly, it has now been found that the release characteristics of a pharmaceutical composition of the present invention comprising diclofenac in its free acid forms can also show fast release characteristics.

In particular, it was shown that a pharmaceutical composition comprising diclofenac in its free acid form can even provide faster release characteristics than comprising diclofenac salts, i.e. sodium or potassium, when first being exposed to a media having a pH around 1.1, such as gastric fluid.

Beyond that and completely unexpected, it has been also found that after exposing to a media having a pH 1.1 (such as gastric fluid) diclofenac acid significantly faster dissolve at pH 6.8 (such as intestinal fluid) than both diclofenac sodium or diclofenac potassium. In this respect, it could be shown that diclofenac sodium and diclofenac potassium but not diclofenac acid form agglomerates at pH 1.1 (such as gastric fluid). The formation of such agglomerates results in slower dissolution rates at pH 6.8. Hence, the use of diclofenac acid instead of diclofenac sodium or diclofenac potassium prevents agglomeration of diclofenac and thereby ensures a faster dissolution in the intestine resulting in a faster absorption and finally in a faster onset of the therapeutics effects of diclofenac.

In one embodiment, the pharmaceutical composition of the invention is composed of granules in which diclofenac or a pharmaceutically acceptable salt thereof and the (meth) acrylic polymer are blended. Such granules typically contain an approximately homogenous mixture of all components. Given that such granules are not provided with a separate coating, it is particularly surprising that they achieve the required taste-masking properties in order to achieve the objects of the invention. Often a coating is used to mask an unpleasant taste of an active ingredient, but such a coating is not used in the pharmaceutical composition composed of granules according to the invention. Nevertheless, a pharmaceutical composition of the present invention composed of the afore-described granules not only releases diclofenac in a suitable manner, but still achieves a superior taste-masking and ensures an advantageous patient compliance. This means that as intended by the invention, the pharmaceutical composition of diclofenac is provided with advantageous patient compliance characteristics, whilst simultaneously ensuring suitable drug release profiles.

For a pharmaceutical composition of the invention, which is composed of granules in which diclofenac or a pharmaceutically acceptable salt thereof and the (meth)acrylic polymer are blended, it is moreover preferable that the relative amount of the (meth)acrylic polymer in the pharmaceutical composition lies in the range of ≥0.1 to ≤10.0 wt. %, based on the total weight of the pharmaceutical composition. A more preferred range is ≥0.5 to ≤8.0 wt. %, with a range of ≥1.0 to ≤4.0 wt. % being even more preferred.

In principle, the pharmaceutical composition of the invention, including the one composed of granules, can be administered orally in any suitable form such as tablets, orally disintegrating tablets, dispersible tablets, effervescent tablets, sachets, stick packs, capsules, inspissated juices and dry suspensions. However, because of an easy handling and a comparably small size, e.g. in comparison to capsules, it is preferable that the pharmaceutical composition of the invention is present in tablet form, i.e. as a tablet, which is a readily administrable dosage form according to the invention.

In a further embodiment, the pharmaceutical composition of the invention is composed of pellets with cores containing said diclofenac or said pharmaceutically acceptable salt thereof, wherein said cores have a coating comprising said (meth)acrylic polymer. Whilst a coating typically contributes to taste-masking properties, as the coating employed in this invention actually does, it is often detrimental to the release properties of a pharmaceutical composition. Unexpectedly, this is not the case for the present pharmaceutical composition cores containing diclofenac or a pharmaceutically acceptable salt of diclofenac, which cores have a coating comprising the (meth)acrylic polymer. The release profiles of diclofenac contained in such a pharmaceutical composition composed of pellets remains particularly suitable. That is, another pharmaceutical composition of diclofenac is provided with advantageous patient compliance characteristics, whilst simultaneously ensuring suitable drug release profiles.

For a pharmaceutical composition of the invention, which is composed of pellets with cores containing said diclofenac or said pharmaceutically acceptable salt thereof, wherein said cores have a coating comprising said (meth)acrylic polymer, it is moreover preferable that the relative amount of the (meth)acrylic polymer in the pharmaceutical composition lies in the range of ≥1.0 to ≤50.0 wt. %, based on the total weight of the pharmaceutical composition. A more preferred range is ≥5.0 to ≤25.0 wt. %, with a range of ≥9.0 to ≤18.0 wt. % being even mote preferred.

For a pharmaceutical composition of the invention, which is composed of pellets with cores containing said diclofenac or said pharmaceutically acceptable salt thereof, wherein said cores have a coating comprising said (meth)acrylic polymer, it is moreover preferable that the pellets have an average particle size in the range from 0.10 to 0.40 mm. It is also preferred that more than 95 wt % of the pellets according to the present invention have a particle size in the range from 0.05 to 0.50 mm. The particle size distribution is determined by sieve analysis.

For the same reasons as given above, it is again preferable that this additional pharmaceutical composition has the form of a tablet.

Tablets made from pharmaceutical compositions of the invention can e.g. be ODTs, i.e. orally disintegrating tablets. It is preferable that such tablets disintegrate in a very short time, in particular within less than 30 seconds, in some cases even within less than 15 seconds.

In one embodiment, the pharmaceutical composition of the invention comprises diclofenac as an active ingredient and a (meth)acrylic polymer having at least one tertiary amino group containing component. Preferably, the (meth) acrylic polymer is soluble in an aqueous medium at a pH value of ≤5.0.

A tertiary amino group is particularly advantageous for achieving improved taste-masking properties since it does not dissolve in the saliva. Therefore, a tertiary amino group prevents the drug to be released from the pharmaceutical composition of the present invention in the mouth before swallowing.

In addition, the (meth)acrylic polymer which is soluble in an aqueous medium at a pH value of ≤5.0, allows that the composition of the present invention release the drug in the gastric environment, i.e. in the stomach. Thus, (meth)acrylic polymer which is soluble in an aqueous medium at a pH value of ≤5.0 ensures that diclofenac particles enter the intestine in a polymer free form. Such a polymer free form allows the diclofenac particles to quickly dissolve in the intestinal medium, which is required to provide rapid absorption and hence, a rapid onset of the therapeutic effects.

Under these conditions it was surprisingly found, that a pharmaceutical composition of the invention comprising diclofenac in the free acid form exhibits improved drug dissolution characteristics compared to a pharmaceutical composition of the invention comprising diclofenac as a pharmaceutically salt, such as, diclofenac sodium or diclofenac potassium. In this context and as already outlined above, it was completely unexpected found that diclofenac particles in a polymer free form behave differently in an acidic medium (such as the gastric fluid with pH 1.1-1.6) depending whether the diclofenac particles are in form of the free acid or in the salt. It was further found that such different behaviour influences the rate and extent of dissolution of diclofenac in the intestine. Therefore, it was surprisingly found that diclofenac acid taste-mask with a (meth)acrylic polymer having at least one tertiary amino group containing component results in a pharmaceutical compositions rapidly effective due to improved release characteristics, i.e. improved disintegration characteristics of the pharmaceutical composition and dissolution characteristics of diclofenac.

In one preferred embodiment of the pharmaceutical composition of the invention comprising diclofenac as an active ingredient and a (meth)acrylic polymer having at least one tertiary amino group containing component, the (meth)acrylic polymer is present in the pharmaceutical composition in an amount in the range of ≥1.0 to ≤20.0 wt. % based on the total weight of the pharmaceutical composition, in particular in an amount in the range of ≥1.0 to ≤10.0 wt. % based on the total weight of the pharmaceutical composition.

The less amounts of the (meth)acrylic polymer are used the faster is the process of manufacturing the pharmaceutical compositions of the present invention. In addition, the less amounts of the (meth)acrylic polymer are used the bioavailability of diclofenac is improved.

As outlined above the bioavailability of diclofenac from solid oral dosage forms is controlled by the rate and extent of disintegration of the solid dosage form in the gastrointestinal tract prior to the dissolution of diclofenac in the intestine. The less amounts of the (meth)acrylic polymer are used the ability of the (meth)acrylic polymer to dissolve in the acidic medium, i.e. in the stomach, is enhanced and thereby disintegration of the pharmaceutical composition of the present invention is more quickly. Hence, diclofenac is faster released from the pharmaceutical composition of the present invention by the use of little amounts of the (meth)acrylic polymer. Hence, little amounts of the (meth)acrylic polymer finally influence the release characteristics of the pharmaceutical compositions.

However, the amount of the (meth)acrylic polymer is limited by taste-masking of diclofenac. In other words reducing the amount of the (meth)acrylic polymer is only possible as far as sufficient taste-masking is ensured. In this respect, it has been surprisingly found, that if the (meth)acrylic polymer is present in the pharmaceutical composition in an amount in the range of ≥1.0 to ≤20.0 wt. % based on the total weight of the pharmaceutical composition, in particular in an amount in the range of ≥1.0 to ≤10.0 wt. % based on the total weight of the pharmaceutical composition, sufficient taste-masking of diclofenac is provided, while at the same time fast release characteristics of the pharmaceutical composition are ensured.

In another preferred embodiment of the pharmaceutical composition of the invention comprising diclofenac as an active ingredient and a (meth)acrylic polymer having at least one tertiary amino group containing component, the diclofenac has a particle size between 1 and 100 µm, especially between 1 and 40 µm, more especially between 5 and 10 µm, i.e. ~7 µm average particle size.

The average particle size influences both: the final amount of polymer needed to sufficiently taste-mask diclofenac and the rate of dissolution. On one hand, a very fine powder, i.e. very small drug particles, is more appropriate to achieve fast release characteristics. Indeed, the smaller the particles are, the higher is their surface of contact with the media into which they have to dissolve. The higher the surface of contact with the media is the faster are their dissolving characteristics.

However, the higher this surface area is, and thus the more they can dissolve, the more they can be tasted. Therefore it is suggested that more polymer amounts should be applied onto these particles, i.e. more mg of polymer per cm² of diclofenac. This effect, however, complicates the taste-masking of very fine powder like diclofenac. High amount of polymer means a longer process and finally heavier/bigger pharmaceutical dosage forms.

It was surprisingly found that with this very fine powder (which allows fast release characteristics), only little amount of polymer is needed, while there still is a sufficient taste-masking effect.

A particle size between 1 and 100 µm, especially between 1 and 40 µm, further allows to sufficiently taste-mask the diclofenac with low amounts of polymer. In particular, a particle size between 1 and 100 µm, especially between 1 and 40 µm, allows reducing the recommended amount for standard coating application by at least 50-90%, preferably 60-90%, more preferably 70-90% and even more preferably, 80-90%.

In a further preferred embodiment of the pharmaceutical composition of the invention comprising diclofenac as an active ingredient and a (meth)acrylic polymer having at least one tertiary amino group containing component, the ratio between (meth)acrylic polymer and diclofenac is between 1:20 and 1:8, especially in the range of 1:15 and 1:9.

It was surprisingly found, that a ratio of 1:20 and 1:8, especially of 1:15 and 1:9 is sufficient to sufficiently task-mask diclofenac. This is surprising because the amount of polymer is about 10 times smaller than the amount of diclofenac. Usually, much more polymer amounts are used to completely cover the API particles, i.e. too sufficiently mask its taste.

In another preferred embodiment of the pharmaceutical composition of the invention comprising diclofenac as an active ingredient and a (meth)acrylic polymer having at least one tertiary amino group containing component, the (meth)acrylic polymer is poly(butyl methacrylate-co-(2-dimethylaminoethyl)methacrylate-co-methyl methacrylate).

In a further preferred embodiment of the pharmaceutical composition of the invention comprising diclofenac as an active ingredient and a (meth)acrylic polymer having at least one tertiary amino group containing component, the ratio of butyl methacrylate to (2-dimethylaminoethyl)methacrylate to methyl methacrylate is in the range of 0.5-2:1-3:1, especially in the range of 0.8-1.2:1.5-2.5:1, and in particular 1:2:1.

In another preferred embodiment of the pharmaceutical composition of the invention comprising diclofenac as an active ingredient and a (meth)acrylic polymer having at least one tertiary amino group containing component, the (meth)acrylic polymer has a weight average molar mass in the range of 40,000 to 54,000 g/mol, especially in the range of 44,000 to 50,000 g/mol, and in particular of 47,000 g/mol.

In a particular preferred embodiment of the pharmaceutical composition of the invention comprising diclofenac as an active ingredient and a (meth)acrylic polymer having at least one tertiary amino group containing component, the diclofenac is the only active ingredient in said pharmaceutical composition.

In one preferred embodiment of the pharmaceutical composition of the invention comprising diclofenac as an active ingredient and a (meth)acrylic polymer having at least one tertiary amino group containing component, the pharmaceutical composition is composed of granules in which said diclofenac and said (meth)acrylic polymer are blended.

In another preferred embodiment of the pharmaceutical composition of the invention comprising diclofenac as an active ingredient and a (meth)acrylic polymer having at least one tertiary amino group containing component, the pharmaceutical composition is composed of pellets with cores containing said diclofenac, wherein said cores have a coating comprising said (meth)acrylic polymer.

One embodiment of the present invention relates to a tablet comprising the pharmaceutical composition of the invention comprising diclofenac as an active ingredient and a (meth)acrylic polymer having at least one tertiary amino group containing component,

DETAILED DESCRIPTION OF EMBODIMENTS

Figure 1:
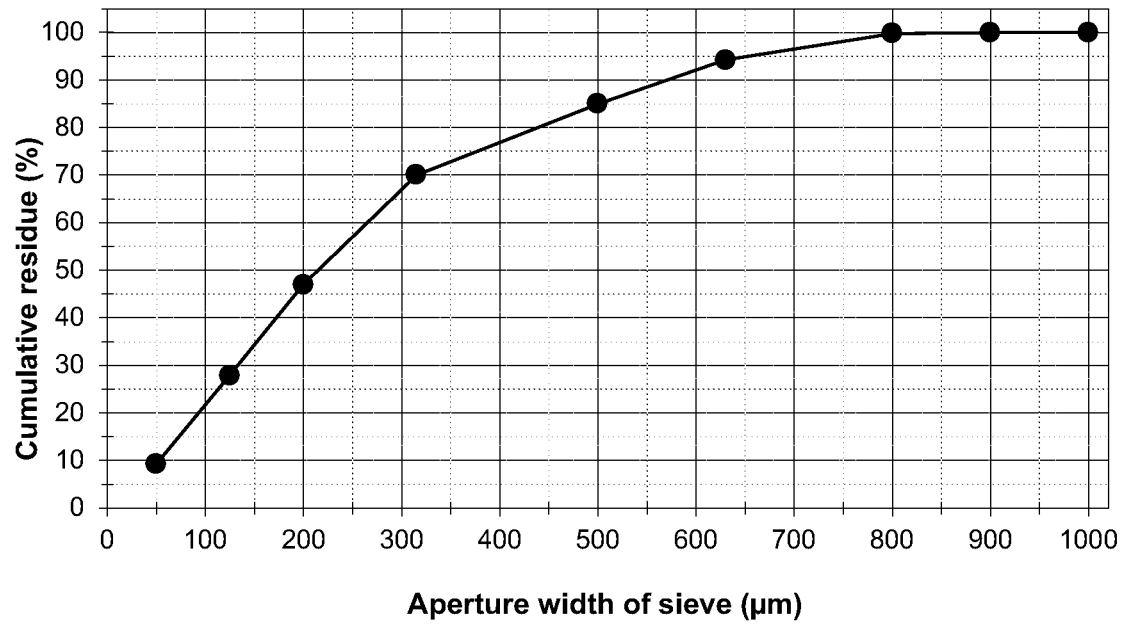
FIG. 1 illustrates the sieve analysis of the diclofenac granulate obtained in Example 1.

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Analytical Methods
Dissolution Performance

Dissolution testing were conducted in accordance with the USP method using dissolution apparatus type II (paddle) Sotax, model AT7 (Sotax, Switzerland) in 1000 ml of buffeted phosphate pH 6.8±0.05 and at 37±0.5° C. temperature. The paddle was driven at 50 rpm rotation speed. The samples for dissolution testing always reflected 23.25 mg diclofenac drug loading. The cumulative drug release was determined online using a UV spectrophotometer Perkin-Elmer Lambda 25 (Perkin-Elmer, USA) operating at 276 nm, after filtration through a glass microfiber filter Whatman GF/D (Whatman, UK). Samples were withdrawn over a 60 minutes period at predetermined time: 5, 10, 15, 20, 30, 45 and 60 minutes respectively.

Assay/Purity
(i) Instrumentation

A liquid chromatography with a Diode Area Detection was used. The HPLC method was performed on a Perkin Elmer (Perkin-Elmer, USA) equipped with a binary pump 200, a diode array detector 235C, an autosampler ISS 200 and a thermostated column.

(ii) Conditions

Diclofenac samples were analyzed using a Xtetra MS C8 5 µm column (5 µm, length 150 mm, internal diameter 3.9 mm) (Waters, USA) and a C8 pre-column Security Guard Cartridge System kit (Phenomenex, Switzerland). The mobile phase comprised a mixture of methanol and phosphate buffer solution pH 2.5±0.05 with 1 ml/min flow rate (isocratic method). The method used a detector wavelength at 254 nm and room column temperature. The injection volume was 30 µl for assay and impurities determination respectively. The chromatogram time was about 6 minutes. Acceptance criteria for assay are in the range of 90.0-110.0%.

Particle Size Distribution

The particle size distribution of the pellets was determined by sieve analysis performed with an Alpine air jet sieve A 200 LS (Hosokawa Alpine, Germany) operating at the following conditions: 10 g/sieve sample size, 1200 Pa vacuum, 2 minutes sieving time. A Mettler PG 4002 S balance was used for weighing the samples.

Tablet Characterisation

The crushing strength of the tablets was determined according to the monograph for hardness testing <1217> of the USP using a Schleuniger 5 Y equipment.

EXAMPLES

The preparation of formulations according to this invention is illustrated by way of practical working examples, without being restricted by them in any manner.

The formulations of all examples have appropriate taste properties.

Example 1

Granulation of the Active Ingredient Diclofenac

According to this invention, granulates of the active ingredient were prepared by suitable granulation processes. Diclofenac was moistened together with suitable excipients in a fast mixer VG 10, Glatt, and the pre-moistened mass was processed into granulates of suitable size, in order to achieve an active ingredient content of about 9.8 wt. %. The granulation was followed by drying in a fluidized bed.

The composition of the basic formulation, which contains the active ingredient diclofenac, is described in the following table. Accordingly, the basic formulation is preferably composed of, apart from the active ingredient, mannitol (Pearlitol 160, Roquette), cross-linked polyvinylpyrrolidone (Kollidon CL, BASF), microcrystalline cellulose (Avicel PH 101, FMC), sucralose (Splenda Sucralose, Tate & Lyle) and hydrogenated vegetable oil (Lubritab, Albert Isliker & Co).

| Basic formulation | Product name, Manufacturer | Mass (g) |
|---|---|---|
| Diclofenac | | 125.00 |
| Mannitol | Pearlitol 160 C, Roquette | 1043.75 |
| Crosslinked polyvinylpyrrolidone | Kollidon CL-M, BASF | 37.50 |
| Microcrystalline cellulose | Avicel PH 101, FMC | 25.00 |
| Sucralose | Splenda Sucralose, Tate&Lyle | 6.25 |
| Hydrogenated vegetable oil | Lubritab, Albert Isliker & Co. | 12.50 |
| Total | | 1250.00 |

The powder mixture indicated in the table was mixed for 2 minutes in a fast mixer VG 10 (Glatt) and moistened with about 250 g of aqueous dispersion by means of a two-substances-nozzle. The composition of the dispersion is described in the following table. Accordingly, the dispersion is preferably composed of methacrylic polymer (Eudragit E PO, Evonik), sodium laurylsulphate (SDS, Fluka), stearic acid (Stearic acid 50, powder, Mallinckrodt), magnesium stearate (Magnesium stearate, Merck), talc (Talc Pharma, Luzenac) and purified water.

| Dispersion formulation | Product name, Manufacturer | Mass (g) |
|---|---|---|
| Methacrylic polymer | Eudragit E PO, Evonik | 14.30 |
| Sodium laurylsulphate | SDS, Fluka | 1.43 |
| Stearic acid | Stearic acid 50, powder, Mallinckrodt | 2.13 |
| Magnesium stearate | Magnesium stearate, Merck | 1.43 |
| Talc | Talc Pharma, Luzenac | 5.71 |
| Pure water | | 225.00 |
| Total | | 250.00 |

For preparing the dispersion, pure water was provided in a suitable stainless steel container. Next, all excipients were dissolved and dispersed, respectively, in a suitable order while stirring. Therefore, sodium laurylsulphate was first dispersed in 150.0 g water with dissolving disk during 5 minutes. Stearic add was then added to the suspension further steered during 5 minutes using an Ultra-Turrax device. Eudragit E PO was incorporated to the suspension and steered with dissolving disk overnight (minimum 6 hours). Afterwards, magnesium stearate and talc were separately dispersed in 75.0 g during 5 minutes using an Ultra-Turrax device. The two suspensions were then mixed together and steered with dissolving disk during 30 minutes. Finally, the dispersion was sieved through a 0.2 mm sieve. The batch was kept being stirred continuously. Afterwards, the granulates were dried at a temperature of 40° C. in the fluidized bed. The LOD value (loss on drying value) was <1% (halogen dryer, Mettler, 105° C., 1 mg/30 s).

The removed granulate had the following grain size distribution (sieve analysis; see also FIG. 1):

| Sieve size (μm) | Cumulative residue (%) |
|---|---|
| 50 | 9.31 |
| 125 | 27.92 |
| 200 | 47.02 |
| 315 | 70.12 |
| 500 | 85.00 |
| 630 | 94.26 |
| 800 | 99.80 |
| 900 | 100.00 |
| 1000 | 100.00 |

The granulation resulted in taste-masked granulates with a grain spectrum between 50 to 700 μm (d50 about 225 μm).

The thus produced diclofenac products had the following content of active ingredient and the following purity:

| Content | |
|---|---|
| Content (wt. %) | 9.8 |
| Theoretical content (%) | 102.03 |

| Purity | | |
|---|---|---|
| Denomination | Unknown | Impurity A |
| Retention time (min) | 2.85 | 2.65 |
| Amount (%) | 0.03 | 0.03 |

Impurity A refers to the cyclic compound 1-(2,6-dichlorophenyl)-1,3-dihydro-2H-indol-2-one described in the European and the United States Pharmacopoeias.

Figure 6:
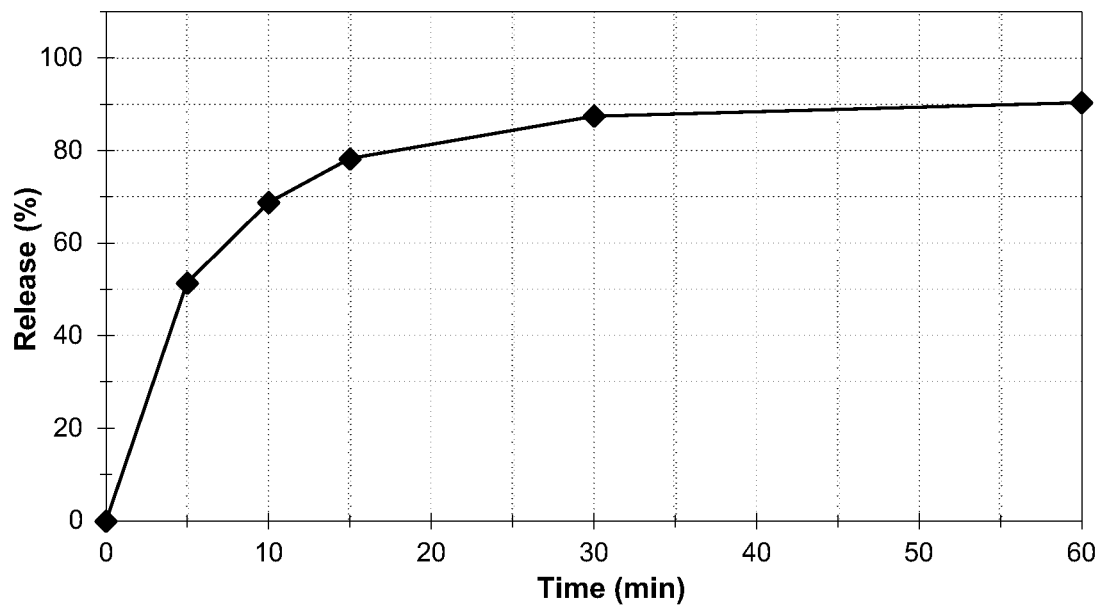
FIG. 6 illustrates the release profile of the diclofenac granulate obtained in Example 1.

The cumulative release of the diclofenac granulate is illustrated in FIG. 6. The actual release profile data is provided in the table below:

| | % dissolved diclofenac | |
|---|---|---|
| Time (min) | Mean value | Standard deviation |
| 0 | 0.0 | 0.0 |
| 5 | 51.5 | 1.4 |
| 10 | 68.8 | 0.4 |
| 15 | 78.3 | 1.0 |
| 30 | 87.5 | 0.9 |
| 60 | 90.4 | 1.0 |

When the release test is conducted in a basic buffer solution, likewise profiles are obtained which show a complete diclofenac release which accords with the specifications of the International Pharmaceutical Federation (FTP) for fast releasing products (at least 80% of the drug substance dissolved in 30 minutes).

Example 2

Granulation of the Active Ingredient Diclofenac

According to this invention granulates of the active ingredient were prepared by suitable granulation processes. Diclofenac was moistened together with suitable excipients in the fast mixer VG 10, Glatt, and the pre-moistened mass was processed into granulates of suitable size, in order to achieve a content of active ingredient of about 47 wt. %. The granulation was followed by drying in the fluidized bed.

The composition of the basic formulation, which contains the active ingredient diclofenac, is described in the following table. Accordingly, the basic formulation is preferably composed of, apart from the active ingredient, microcrystalline cellulose (Avicel PH 101, FMC) and crosslinked polyvinylpyrrolidone (Kollidon CL, BASF).

| Basic formulation | Product name, Manufacturer | Mass (g) |
|---|---|---|
| Diclofenac | | 500.0 |
| Microcrystalline cellulose | Avicel PH 101, FMC | 400.0 |
| Crosslinked polyvinylpyrrolidone | Kollidon CL-M, BASF | 100.0 |
| Total | | 1000.0 |

The powder mixture shown in the table was mixed for 2 minutes in the fast mixer VG 10 (Glatt) and was moistened with about 650 g of an aqueous dispersion by means of a two-substances-nozzle. The composition of the dispersion is described in the following table. Accordingly, the dispersion is preferably composed of methacrylic polymer (Eudragit E PO, Evonik), sodium laurylsulphate (SDS, Fluka), stearic acid (Stearic acid 50, powder, Mallinckrodt), magnesium stearate (Magnesium stearate, Merck), talc (Talc Pharma, Luzenac) and purified water.

| Dispersion formulation | Product name, Manufacturer | Mass (g) |
|---|---|---|
| Methacrylic polymer | Eudragit E PO, Evonik | 37.10 |
| Sodium laurylsulphate | SDS, Fluka | 3.71 |
| Stearic acid | Stearic acid 50, powder, Mallinckrodt | 5.60 |
| Magnesium stearate | Magnesium stearate, Merck | 3.71 |
| Talc | Talc Pharma, Luzenac | 14.88 |
| Pure water | | 585.00 |
| Total | | 650.00 |

For preparing the dispersion pure water was provided in a suitable stainless steel container. Next, all excipients were dissolved and dispersed, respectively, in a suitable order whilst stirring. In the end, the dispersion was sieved through a 0.2 mm sieve. The batch was kept being stirred continuously.

Afterwards, the granulates were dried at a temperature of 40° C. in the fluidized bed. The LOD value was <1% (halogen dryer, Mettler, 105° C., 1 mg/30 s).

Figure 2:
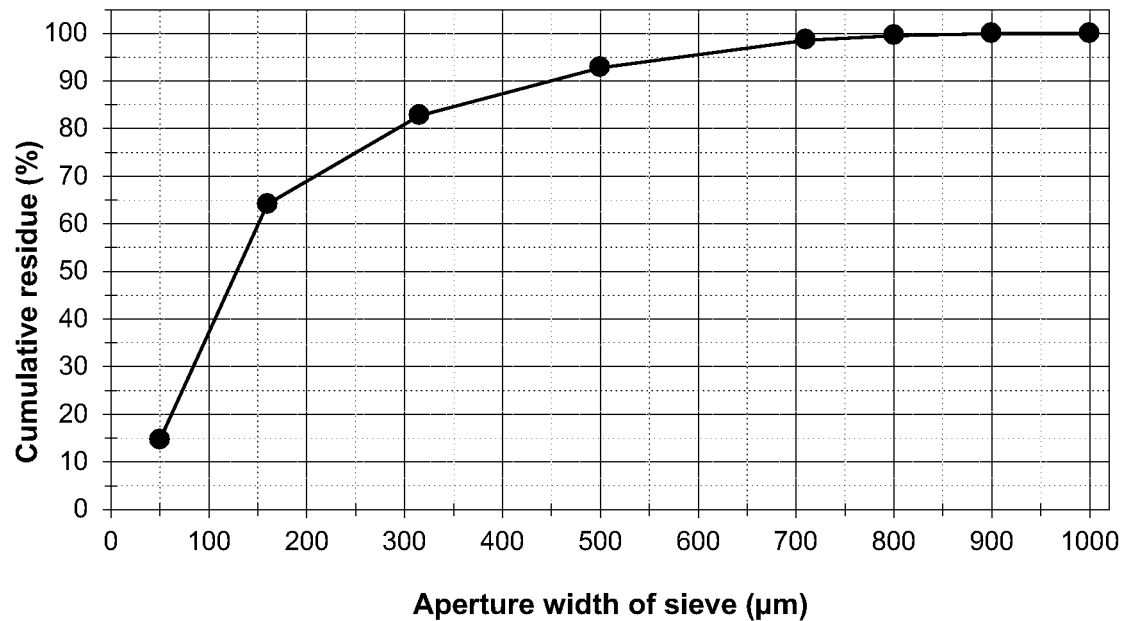
FIG. 2 illustrates the sieve analysis of the diclofenac granulate obtained in Example 2.

The removed granulate had the following grain size distribution (sieve analysis; see also FIG. 2):

| Sieve size (µm) | Cumulative residue (%) |
|---|---|
| 50 | 14.71 |
| 160 | 64.20 |
| 315 | 82.80 |
| 500 | 92.83 |
| 710 | 98.61 |
| 800 | 99.60 |
| 900 | 100.00 |
| 1000 | 100.00 |

The granulation resulted in taste-masked granulates having a grain spectrum between 50 to 600 µm (d50 about 125 µm). The thus produced diclofenac products had the following content of active ingredient and the following purity:

| Content | | | |
|---|---|---|---|
| Content (wt. %) | | | 46.95 |
| Theoretical content (%) | | | 102.78 |
| Purity | | | |
| Denomination | Unknown | Unknown | Impurity A |
| Retention tune (min) | 3.00 | 3.36 | 2.67 |
| Amount (%) | 0.03 | 0.03 | 0.04 |

Figure 7:
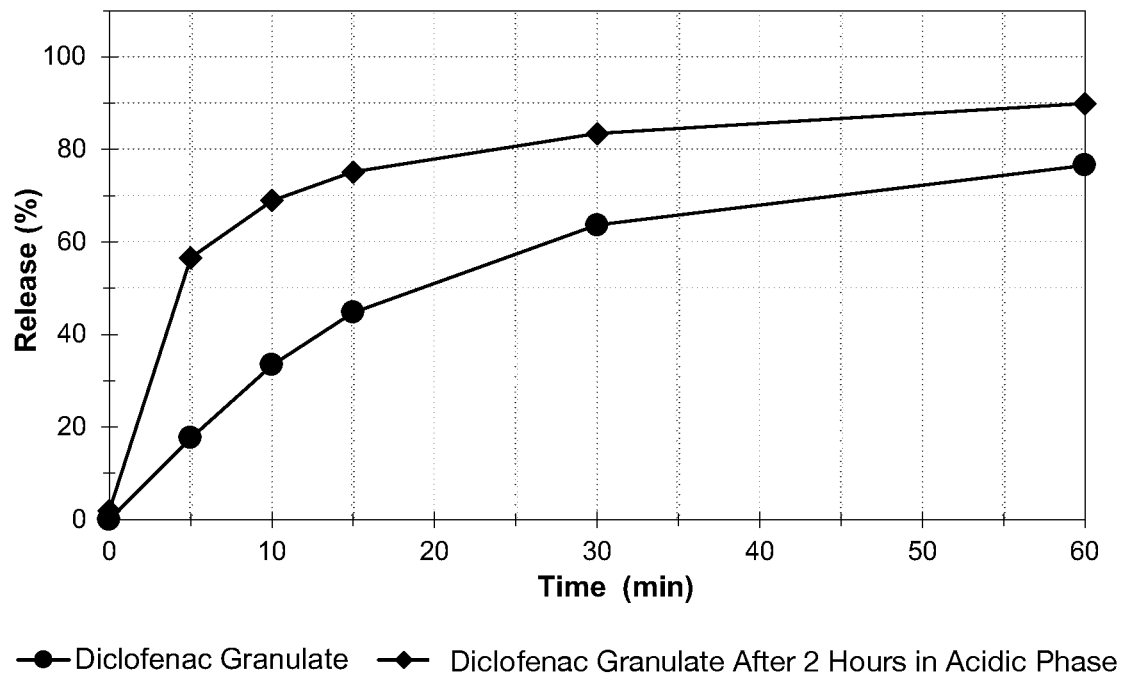
FIG. 7 illustrates the release profile of the diclofenac granulate obtained in Example 2.

The cumulative release of the diclofenac granulates is illustrated in FIG. 7. The actual release profile data is provided in the table below:

| | % dissolved diclofenac | |
|---|---|---|
| Time (min) | Mean value | Standard deviation |
| 0 | 0.0 | 0.0 |
| 5 | 17.7 | 0.8 |
| 10 | 33.5 | 2.5 |
| 15 | 44.8 | 2.9 |
| 30 | 63.7 | 1.8 |
| 60 | 76.6 | 4.2 |

| | % dissolved diclofenac after 2 h in 0.1N HCl, pH 1.1 | |
|---|---|---|
| Time (min) | Mean value | Standard deviation |
| 0 | 2.0 | 0.5 |
| 5 | 56.7 | 2.9 |
| 10 | 69.0 | 2.4 |
| 15 | 75.2 | 2.6 |
| 30 | 83.4 | 3.4 |
| 60 | 90.0 | 4.1 |

When granulated with Eudragit E PO, the cumulative release of diclofenac in the buffer phase after 60 minutes was about 75%. In the acidic phase, the excipient is dissolved. In that case the release of the active ingredient occurs in the subsequent buffet phase.

Example 3

Granulation/Spheronization of the Active Ingredient Diclofenac and Coating of Produced Pellets Stage 1: Granulation/Spheronization of the Active Ingredient Diclofenac According to this invention active ingredient pellets were prepared by suitable granulation procedures. Diclofenac was moistened together with suitable excipients in the fast mixer VG 10, Glatt and the pre-moistened mass was processed into pellets of suitable size in the rotor fluidized bed, in order to achieve a content of the active ingredient of about 50%. The spheronization was followed by drying in the fluidized bed.

The composition of the core formulation, which contains the active ingredient diclofenac, is described in the following table. Accordingly, the core is preferably composed of apart from the active ingredient, microcrystalline cellulose (Avicel PH 101, FMC).

| Core formulation | Product name, Manufacturer | Mass (g) |
| --- | --- | --- |
| Diclofenac | | 500.00 |
| Microcrystalline cellulose | Avicel PH 101, FMC | 500.00 |
| Total | | 1000.0 |

The powder mixture indicated in the table was mixed in the fast mixer VG 10 (Glatt) for 2 minutes and was moistened with purified water by means of a 1.2 mm two-substances-nozzle. The process parameters are described below.

| Pre-moistening (Glatt VG) | |
| --- | --- |
| Impeller/Chopper number of revolutions | 100/2000 rpm |
| Spray pressure | 0.5 bar |
| Spray rate | 20 ± 5 g/min |
| Amount of water | 450.0 g |
| Loss on drying | about 15% |

After the moistening the mass exhibits a loss on drying of about 15% (determined using the Mettler halogen dryer). The thus pre-moistened mass is then spheronized whilst being sprayed with purified water in the rotor fluidized bed, in the blade rotor CPS 3, Glatt, to pellets and is dried in the fluidized bed (GPCG 1, Glatt). The LOD value was <1% (halogen dryer, Mettler, 105° C., 1 mg/30 s).

| Spheronization (Glatt CPS 3) | |
| --- | --- |
| Rotor plate, angle | 45° |
| Number of blades | 4 flat blades |
| Temperature of supply air | 35 ± 2° C. |
| Volume of supply air | 40 ± 10 m³/h |
| Rotor speed at the spray stage | 800 ± 100 rpm |
| Spray rate | 25 ± 5 g/min |
| Amount of water | 200.0 g |
| Rotor speed during final spheronization | 1200 ± 100 rpm |
| Loss on drying after spheronization | about 35% |
| Drying (Glatt GPCG 1) | |
| Temperature of supply air | 60 ± 5° C. |
| Volume of supply air | 120 ± 20 m³/h |
| Product temperature at end of drying | 40 ± 1° C. |
| Loss on drying after the drying | 0.68% |

Figure 3:
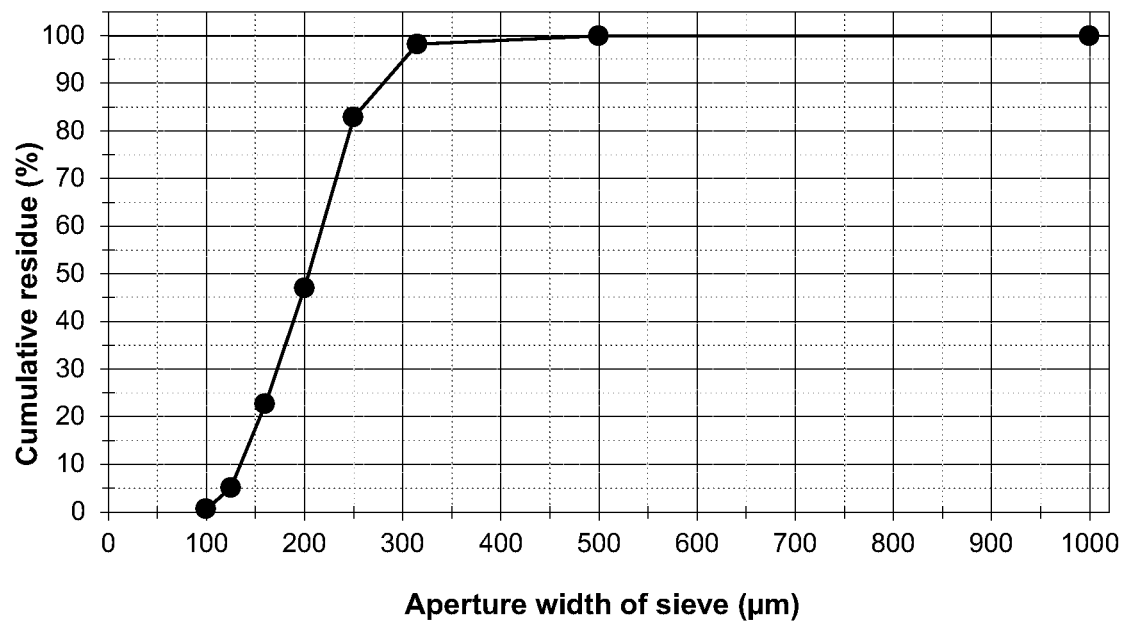
FIG. 3 illustrates the sieve analysis of the diclofenac pellets obtained in stage 1 of Example 3.

The removed granulate had the following grain size distribution (sieve analysis; see also FIG. 3):

| Sieve size (μm) | Cumulative residue (%) |
| --- | --- |
| 100 | 0.60 |
| 125 | 5.08 |
| 160 | 22.67 |
| 200 | 47.04 |
| 250 | 82.94 |
| 315 | 98.20 |
| 500 | 100.00 |
| 1000 | 100.00 |

The drying resulted in pellets having a grain spectrum between 100 to 300 μm (d50 about 200 μm).

The thus produced diclofenac products had the following content of active ingredient and the following purity:

| Content | |
| --- | --- |
| Content (wt. %) | 50.00 |
| Theoretical content (%) | 101.00 |
| Purity | |
| Denomination | Impurity A |
| Retention time (min) | 2.63 |
| Amount (%) | 0.03 |

Stage 2a: Coating of Produced Pellets with an Aqueous Dispersion 1000 g of the above-described diclofenac pellets were afterwards coated in the fluidized bed (GPCG1, Glatt) with a 20% aqueous dispersion of methacrylic polymer (Eudragit E PO). The composition of the dispersion is described in the following table.

| Dispersion formulation | Product name, Manufacturer | Mass (g) |
| --- | --- | --- |
| Methacrylic polymer | Eudragit E PO, Evonit | 114.30 |
| Sodium laurylsulphate | SDS, Fluka | 11.43 |
| Stearic acid | Stearic acid 50, powder, Mallinckrodt | 17.14 |
| Magnesium stearate | Magnesium stearate, Merck | 11.43 |
| Talc | Talc Pharma, Luzenac | 45.70 |
| Pure water | | 1800.00 |
| Total | | 2000.00 |

For that purpose, pure water was provided in a suitable stainless steel container and all excipients were dissolved and dispersed, respectively, in a suitable order whilst stirring. Next, the dispersion was sieved through a 0.2 mm sieve. The batch was kept being stirred continuously. The fluidized bed device with a mounted 6" Wurster-insert was filled with the diclofenac pellets and afterwards sprayed with the dispersion at a temperature of the supply air of about 55±5° C. and a spray pressure of about 1.5 bar. The amount of air at the spray stage is about 50±10 m³/h. The product temperature was about 30° C. The spray rate was mainly about 5 to 10 g/min. Next, the coated pellets were dried at a product temperature of 40° C. for about 20 minutes. The LOD value of the dried pellets was <1% (halogen dryer, Mettler, 105° C., 1 mg/30 s).

Figure 4:
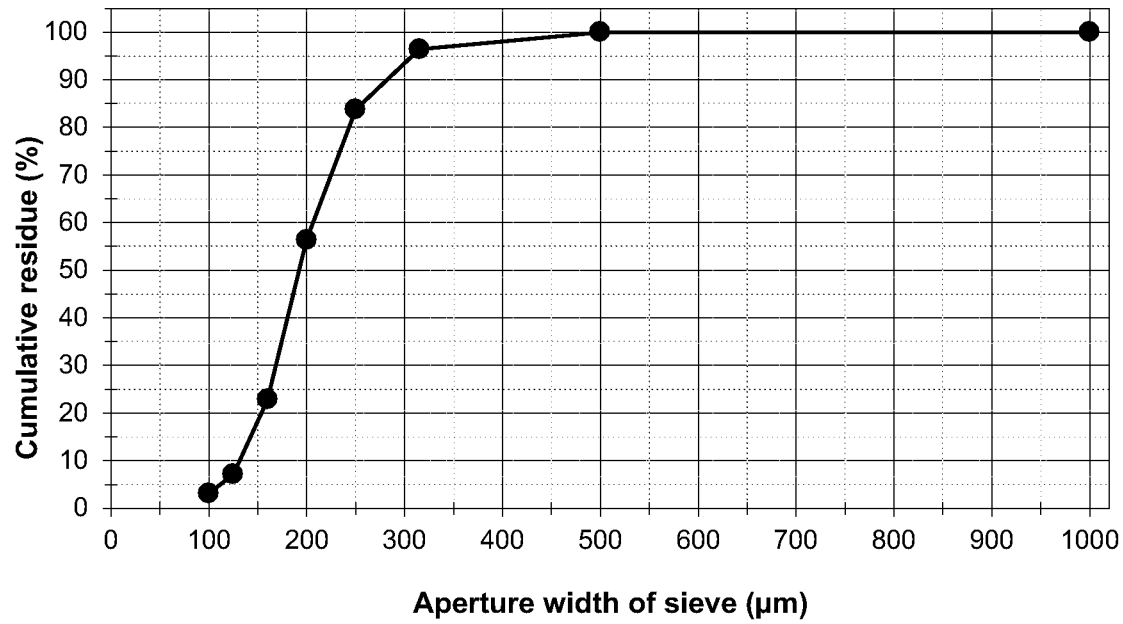
FIG. 4 illustrates the sieve analysis of the diclofenac pellets obtained in stage 2a of Example 3.

The coating resulted in taste-masked pellets having a grain spectrum between 100 to 315 μm (d50 about 190 μm; see also FIG. 4).

| Sieve size (μm) | Cumulative residue (%) |
| --- | --- |
| 100 | 3.18 |
| 125 | 7.18 |
| 160 | 22.85 |
| 200 | 56.41 |
| 250 | 83.76 |
| 315 | 96.42 |
| 500 | 100.00 |
| 1000 | 100.00 |

The thus produced diclofenac products had the following content of active ingredient and the following purity:

| Content | |
| --- | --- |
| Content (wt. %) | 41.67 |
| Theoretical content (%) | 98.65 |

| Purity | |
| --- | --- |
| Denomination | Impurity A |
| Retention time (min) | 2.70 |
| Amount (%) | 0.03 |

Figure 8:
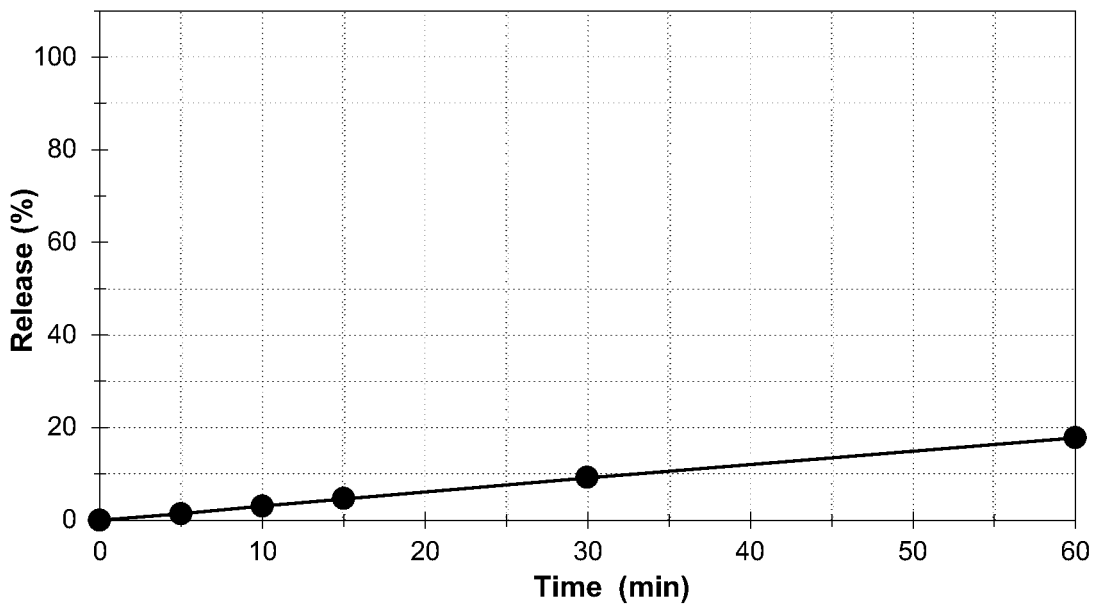
FIG. 8 illustrates the release profile of the diclofenac pellets obtained in stage 2a of Example 3.

The cumulative release of the diclofenac pellets is illustrated in FIG. 8. The actual release profile data is provided in the table below:

| | % dissolved diclofenac | |
| --- | --- | --- |
| Time (min) | Mean value | Standard deviation |
| 0 | 0.0 | 0.0 |
| 5 | 1.4 | 0.3 |
| 10 | 3.0 | 0.6 |
| 15 | 4.6 | 0.5 |
| 30 | 9.2 | 0.2 |
| 60 | 17.8 | 0.9 |

When granulated with Eudragit E PO, the cumulative diclofenac release in the buffer phase 60 minutes was about 20%. In the acidic phase, the excipient would dissolve. In that case the release of the active ingredient would occur in the subsequent buffer phase.

Stage 2b: Coating of Produced Pellets with an Organic Dispersion 1000 g of the above described diclofenac pellets (from stage 1) were afterwards coated in the fluidized bed (GCPG1, Glatt) with a 20% organic dispersion of methacrylic polymer (Eudragit E 12.5). The composition of the dispersion is shown in the following table.

| Dispersion formulation | Product name, Manufacturer | Mass (g) |
| --- | --- | --- |
| Methacrylic polymer dispersion | Eudragit E 12.5 dispersion, Evonik | 1066.70 |
| Magnesium stearate | Magnesium stearate, Merck | 13.30 |
| Talc | Talc Pharma, Luzenac | 53.30 |
| Acetone | | 866.70 |
| Total | | 2000.00 |

For that purpose, acetone was provided in a suitable stainless steel container and all solid excipients were dissolved and dispersed, respectively, in a suitable order whilst stirring. Therefore, magnesium stearate and talc were dispersed in acetone using an Ultra-Turrax device. Thereafter a dispersion of Eudragit E 12.5 was added to it. Afterwards the dispersion was sieved through a 0.2 mm sieve. The batch was kept being stirred continuously. The fluidized bed device with a mounted 6" Wurster-insert was filled with diclofenac pellets and then sprayed with the dispersion at a temperature of the supply air of about 40±5° C. and a spray pressure of about 1.5 bar. The amount of air at the spray stage was about 40±10 m³/h. The product temperature was about 30° C. The spray rate was mainly about 5 g/min. Finally, the coated pellets were dried at a product temperature of 40° C. for about 20 minutes. The LOD value of the dried pellets was <1% (Halogen dryer, Mettler, 105° C., 1 mg/30 s).

Figure 5:
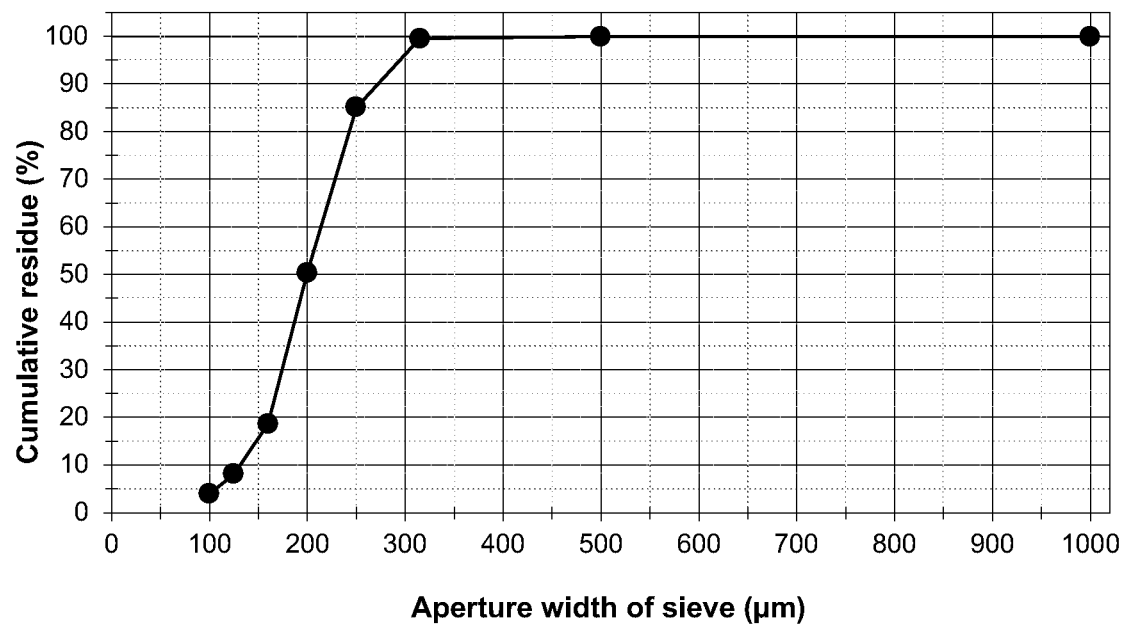
FIG. 5 illustrates the sieve analysis of the diclofenac pellets obtained in stage 2b of Example 3.

The coating resulted in taste-masked pellets having a grain spectrum between 100 to 315 μm (d50 about 200 μm; see also FIG. 5)

| Sieve size (μm) | Cumulative residue (%) |
| --- | --- |
| 100 | 3.99 |
| 125 | 8.09 |
| 160 | 18.69 |
| 200 | 50.30 |
| 250 | 85.13 |
| 315 | 99.60 |
| 500 | 100.00 |
| 1000 | 100.00 |

The thus produced diclofenac products had the following content of active ingredient and the following purity:

| Content | |
| --- | --- |
| Content (wt. %) | 41.67 |
| Theoretical content (%) | 108.31 |

| Purity | |
| --- | --- |
| Denomination | Impurity A |
| Retention time (min) | 2.90 |
| Amount (%) | 0.03 |

Figure 9:
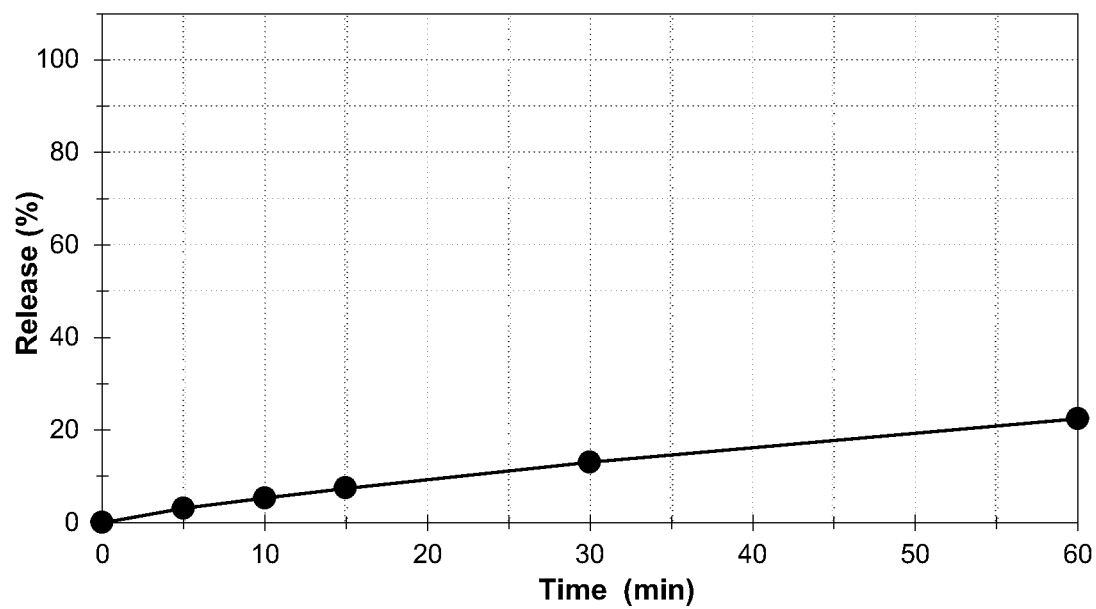
FIG. 9 illustrates the release profile of the diclofenac pellets obtained in stage 2b of Example 3.

The cumulative release of the diclofenac pellets is illustrated in FIG. 9. The actual release profile data is provided in the table below:

| | % dissolved diclofenac | |
| --- | --- | --- |
| Time (min) | Mean value | Standard deviation |
| 0 | 0.0 | 0.0 |
| 5 | 3.1 | 0.2 |
| 10 | 5.3 | 0.1 |
| 15 | 7.5 | 0.3 |
| 30 | 13.1 | 0.5 |
| 60 | 22.5 | 0.8 |

When granulated with Eudragit E PO, the cumulative diclofenac release in the buffer phase after 60 minutes was about 20%. In the acidic phase, the excipient would dissolve. In that case the release of the active ingredient would occur in the subsequent buffer phase.

Example 4

Processing of Diclofenac Granulates into Tablets which Disintegrate Rapidly in the Mouth (Orally Disintegrating Tablets, ODTs)

The active ingredient formulations produced in Example 1 could be pressed into tablets of different dosing strength, here 23.25 mg of active ingredient. The diclofenac granules were premixed together with suitable excipients and the premixed mass was pressed into tablets using an eccentric press (EK0, Korsch).

The mixture was filled into the eccentric press mounted with a 10 mm die and was afterwards compressed with a pressing force of 6 kN. The compression resulted in tablets with a weight of about 250 mg, a hardness between 20 to 30 N and a height of about 2.8 mm. According to the disintegration test, the tablets disintegrated after about 26 seconds. The tablets were neutral in flavour. The quantitative composition of the formulation is described below:

| Formulation | Product name, Manufacturer | Mass (mg/tablet) | (wt. %) |
|---|---|---|---|
| Diclofenac granulate | from Example 1 | 238.20 | 96.50 |
| Talc | Talc Pharma, Luzenac | 3.71 | 1.50 |
| Silicon dioxide | Syloid 244 FP, Grace Davison | 2.46 | 1.00 |
| Sodium stearyl fumarate | Pruv, JRS Pharma | 2.46 | 1.00 |
| Total | | 246.83 | 100.00 |

The thus produced diclofenac products had the following content of active ingredient and the following purity:

| Content | |
|---|---|
| Content (wt. %) | 9.30 |
| Theoretical content (%) | 106.51 |

| Purity | | | |
|---|---|---|---|
| Denomination | Unknown | Unknown | Impurity A |
| Retention time (min) | 3.00 | 3.36 | 2.90 |
| Amount (%) | 0.03 | 0.04 | 0.04 |

Figure 10:
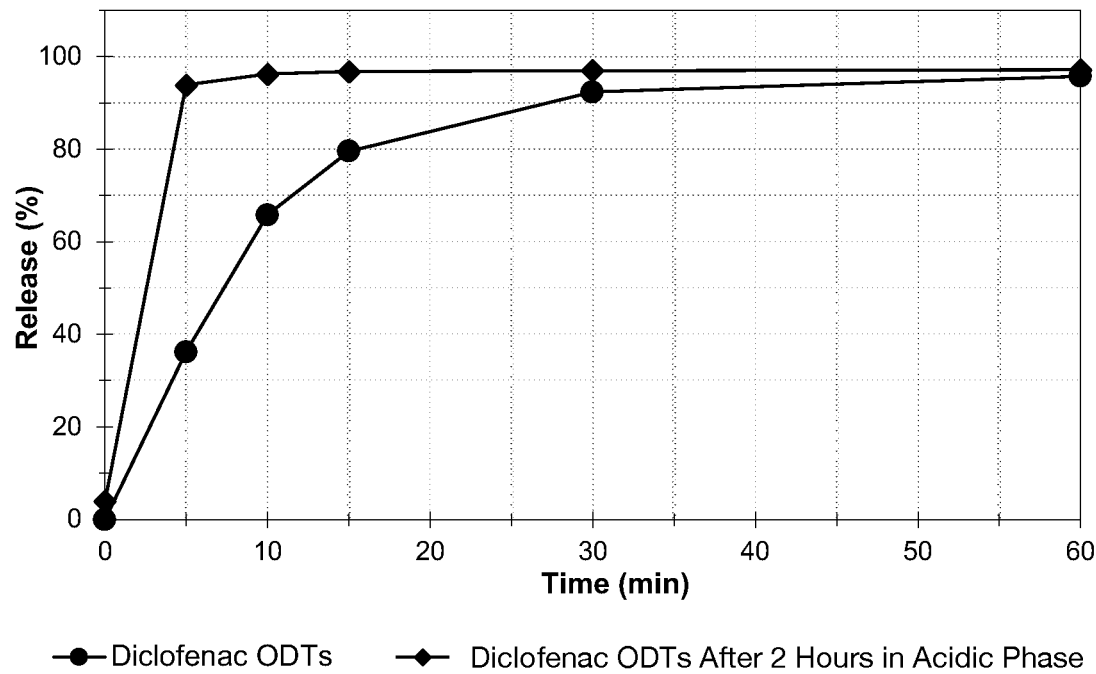
FIG. 10 illustrates the release profile of the diclofenac orally disintegrating tablets (ODTs) obtained in Example 4.

The cumulative release of the diclofenac ODTs is illustrated in FIG. 10. The actual release profile data is provided in the table below:

| % dissolved diclofenac | | |
|---|---|---|
| Time (min) | Mean value | Standard deviation |
| 0 | 0.0 | 0.0 |
| 5 | 36.2 | 6.0 |
| 10 | 65.9 | 2.8 |
| 15 | 79.6 | 1.0 |
| 30 | 92.4 | 0.4 |
| 60 | 95.8 | 0.5 |

| % dissolved diclofenac after 2 h in 0.1N HCl, pH 1.1 | | |
|---|---|---|
| Time (min) | Mean value | Standard deviation |
| 0 | 4.0 | 0.2 |
| 5 | 93.9 | 1.0 |
| 10 | 96.3 | 0.2 |
| 15 | 96.9 | 0.2 |
| 30 | 97.0 | 0.4 |
| 60 | 97.2 | 0.5 |

When granulated with Eudragit E PO, the cumulative diclofenac release in the buffer phase after 60 minutes was 100%. In the acidic phase, the excipient dissolves. In that case the release of the active ingredient occurs in the subsequent buffer phase.

Example 5

Processing of Diclofenac Granulates into Tablets which Disintegrate Rapidly in the Mouth The active ingredient formulations produced in Example 2 could be compressed into tablets of different dosing strength, here 23.25 mg of active ingredient. The diclofenac granules were premixed together with suitable excipients, and the premixed mass was pressed into tablets using an eccentric press (EK0, Korsch).

The mixture was filled into the eccentric press with a mounted 10 mm die and was afterwards compressed with a pressing force of 8.5 kN. The compression resulted in tablets with a weight of about 250 mg, a hardness between 20 to 30 N and a height of about 2.7 mm. According to the disintegration test, the tablets disintegrated after about 13 seconds. The tablets were neutral in flavour. The quantitative composition of the formulation is described below:

| Formulation | Product name, Manufacturer | Mass (mg/tablet) | (wt. %) |
|---|---|---|---|
| Diclofenac pellets | from Example 2 | 49.53 | 19.81 |
| Mannitol | Pearlitol 160 C, Roquette | 179.22 | 71.69 |
| Croscarmellose sodium | Ac-Di-Sol, FMC | 7.50 | 3.00 |
| Microcrystalline cellulose | Avicel PH 101, FMC | 5.00 | 2.00 |
| Talc | Talc Pharma, Luzenac | 2.50 | 1.00 |
| Sucralose | Splenda Sucralose, Tate&Lyle | 1.25 | 0.50 |
| Silicon dioxide | Syloid 244 FP, Grace Davison | 2.50 | 1.00 |
| Sodium stearyl fumarate | Pruv, JRS Pharma | 2.50 | 1.00 |
| Total: | | 250.00 | 100.00 |

The thus produced diclofenac products had the following content of active ingredient and the following purity:

| Content | |
|---|---|
| Content (wt. %) | 9.30 |
| Theoretical content (%) | 102.59 |

| Purity | | | |
|---|---|---|---|
| Denomination | Unknown | Unknown | Impurity A |
| Retention time (min) | 2.9 | 3.2 | 2.65 |
| Amount (%) | 0.02 | 0.03 | 0.05 |

Figure 11:
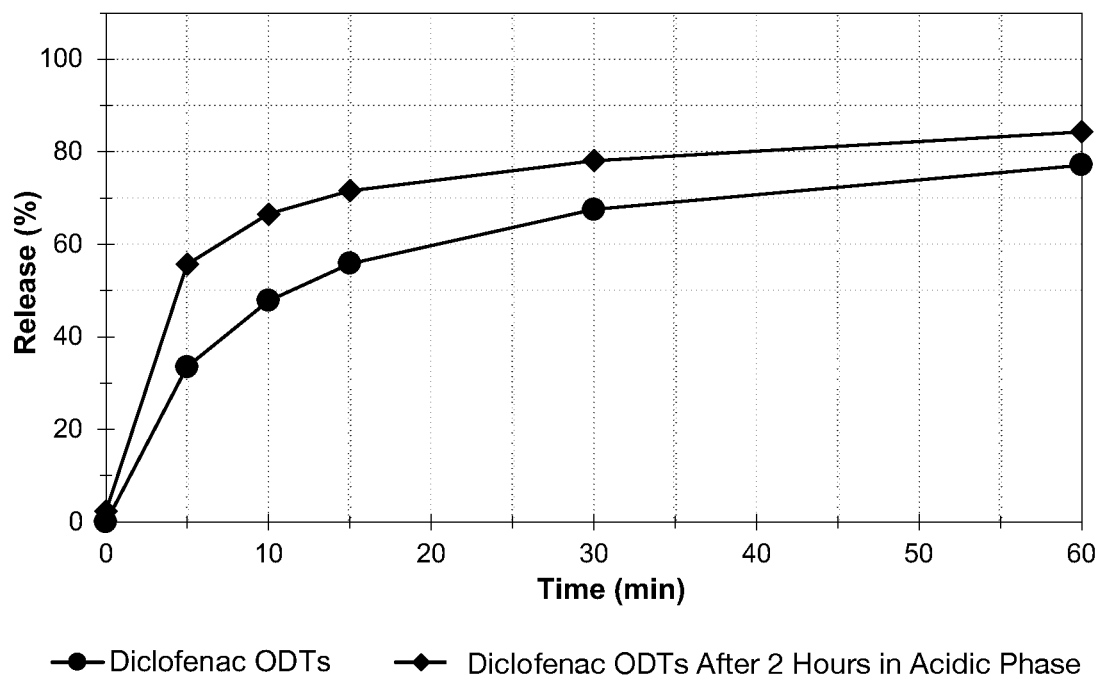
FIG. 11 illustrates the release profile of the diclofenac orally disintegrating tablets (ODTs) obtained in Example 5.

The cumulative release of the diclofenac ODTs is illustrated in FIG. 11. The actual release profile data is provided in the table below:

| % dissolved diclofenac | | |
|---|---|---|
| Time (min) | Mean value | Standard deviation |
| 0 | 0.0 | 0.0 |
| 5 | 33.6 | 1.5 |
| 10 | 47.9 | 1.4 |
| 15 | 55.9 | 2.1 |
| 30 | 67.6 | 2.2 |
| 60 | 77.1 | 3.2 |

| % dissolved diclofenac after 2 h in 0.1N HCl, pH 1.1 | | |
| --- | --- | --- |
| Time (mm) | Mean value | Standard deviation |
| 0 | 2.4 | 0.3 |
| 5 | 55.8 | 2.4 |
| 10 | 66.6 | 2.1 |
| 15 | 71.7 | 2.0 |
| 30 | 78.2 | 2.4 |
| 60 | 84.3 | 2.8 |

When granulated with Eudragit E PO, the cumulative diclofenac release in the buffer phase after 60 minutes was about 78%. In the acidic phase, the excipient dissolves. In that case the release of the active ingredient occurs in the subsequent buffer phase.

Example 6

Processing of Diclofenac Pellets into Tablets which Disintegrate Rapidly in the Mouth The active ingredient formulations produced in Example 3a could be pressed into tablets of different dosing strength, here 23.25 mg of active ingredient. The diclofenac pellets were premixed together with suitable excipients, and the premixed mass was pressed into tablets using an eccentric press (EK0, Korsch).

The mixture was filled into the eccentric press with a mounted 10 mm die and was afterwards compressed with a pressing force of 7.8 kN. The compression resulted in tablets with a weight of about 250 mg, a hardness between 20 to 30 N and a height of about 2.7 mm. According to the disintegration test, the tablets disintegrated after about 14 seconds. The tablets were neutral in flavour. The quantitative composition of the formulation is described below:

| Formulation | Product name, Manufacturer | Mass (mg/tablet) | (wt. %) |
| --- | --- | --- | --- |
| Diclofenac pellets | from Example 3a | 55.80 | 22.32 |
| Mannitol | Pearlitol 160 C, Roquette | 172.95 | 69.18 |
| Croscarmellose sodium | Ac-Di-Sol, FMC | 7.50 | 3.00 |
| Microcrystalline cellulose | Avicel PH 101, FMC | 5.00 | 2.00 |
| Talc | Talc Pharma, Luzenac | 2.50 | 1.00 |
| Sucralose | Splenda Sucralose, Tate&Lyle | 1.25 | 0.50 |
| Silicon dioxide | Syloid 244 FP, Grace Davis on | 2.50 | 1.00 |
| Sodium stearyl fumarate | Pruv, JRS Pharma | 2.50 | 1.00 |
| | Total: | 250.00 | 100.00 |

The thus produced diclofenac products had the following content of active ingredient and the following purity:

| Content | |
| --- | --- |
| Content (wt. %) | 9.30 |
| Theoretical content (%) | 104.74 |

| Purity | |
| --- | --- |
| Denomination | Impurity A |
| Retention time (min) | 3.01 |
| Amount (%) | 0.04 |

Figure 12:
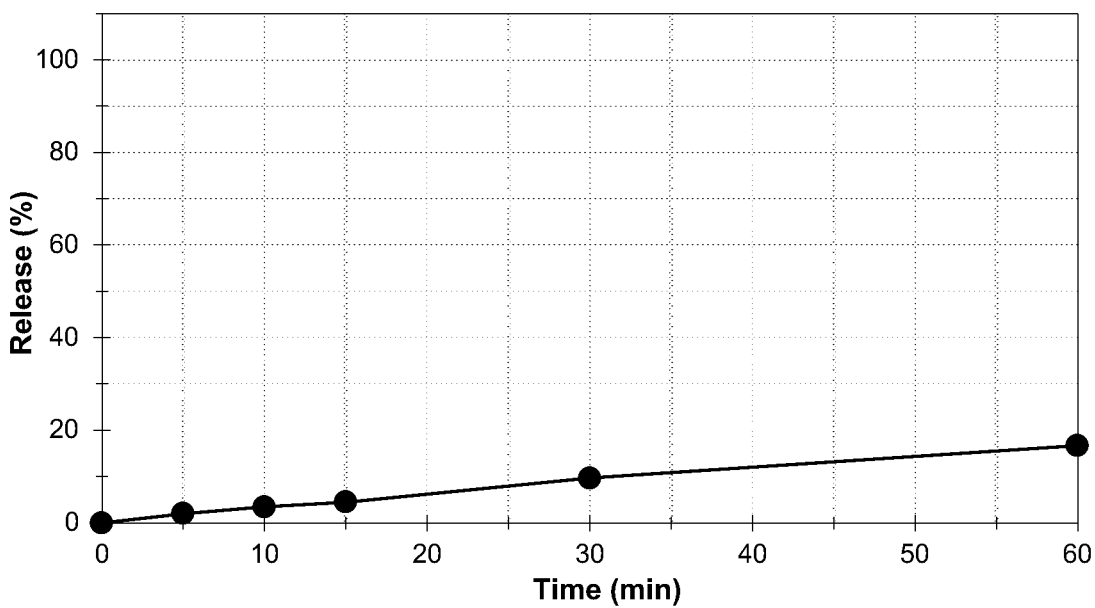
FIG. 12 illustrates the release profile of the diclofenac orally disintegrating tablets (ODTs) obtained in Example 6.

The cumulative release of the diclofenac ODTs is illustrated in FIG. 12. The actual release profile data is provided in the table below:

| % dissolved diclofenac | | |
| --- | --- | --- |
| Time (min) | Mean value | Standard deviation |
| 0 | 0.0 | 0.0 |
| 5 | 2.0 | 0.5 |
| 10 | 3.4 | 0.7 |
| 15 | 4.5 | 0.9 |
| 30 | 9.7 | 1.2 |
| 60 | 16.7 | 1.8 |

When granulated with Eudragit E PO, the cumulative diclofenac release in the buffer phase after 60 minutes was about 18%. In the acidic phase, the excipient would dissolve. In that case the release of the active ingredient would occur in the subsequent buffer phase.

Example 7

Processing of Diclofenac Pellets into Tablets which Disintegrate Rapidly in the Mouth The active ingredient formulations produced in Example 3b could be pressed into tablets of different dosing strength, here 23.25 mg active ingredient. The diclofenac pellets were premixed together with suitable excipients and the premixed mass was pressed into tablets using an eccentric press (EK0, Korsch).

The mixture was filled into the eccentric press with a mounted 10 mm die and was afterwards compressed with a pressing force of 7.2 kN. The compression resulted in tablets with a weight of about 250 mg, a hardness between 20 to 30 N and a height of about 2.7 mm. According to the disintegration test, the tablets disintegrated after about 12 seconds. The tablets were neutral in flavour. The quantitative composition of the formulation is described below:

| Formulation | Product name, Manufacturer | Mass (mg/tablet) | (wt. %) |
| --- | --- | --- | --- |
| Diclofenac pellets | from Example 3b | 55.80 | 22.32 |
| Mannitol | Pearlitol 160 C, Roquette | 172.95 | 69.18 |
| Croscarmellose sodium | Ac-Di-Sol, FMC | 7.50 | 3.00 |
| Microcrystalline cellulose | Avicel PH 101, FMC | 5.00 | 2.00 |
| Talc | Talc Pharma, Luzenac | 2.50 | 1.00 |
| Sucralose | Splenda Sucralose, Tate&Lyle | 1.25 | 0.50 |
| Silicon dioxide | Syloid 244 FP, Grace Davison | 2.50 | 1.00 |
| Sodium stearyl fumarate | Pruv, JRS Pharma | 2.50 | 1.00 |
| | Total: | 250.00 | 100.00 |

The thus produced diclofenac products had the following content of active ingredient and the following purity:

| Content | |
| --- | --- |
| Content (wt. %) | 9.30 |
| Theoretical content (%) | 108.69 |

| Purity | |
| --- | --- |
| Denomination | Impurity A |
| Retention time (min) | 2.95 |
| Amount (%) | 0.03 |

Figure 13:
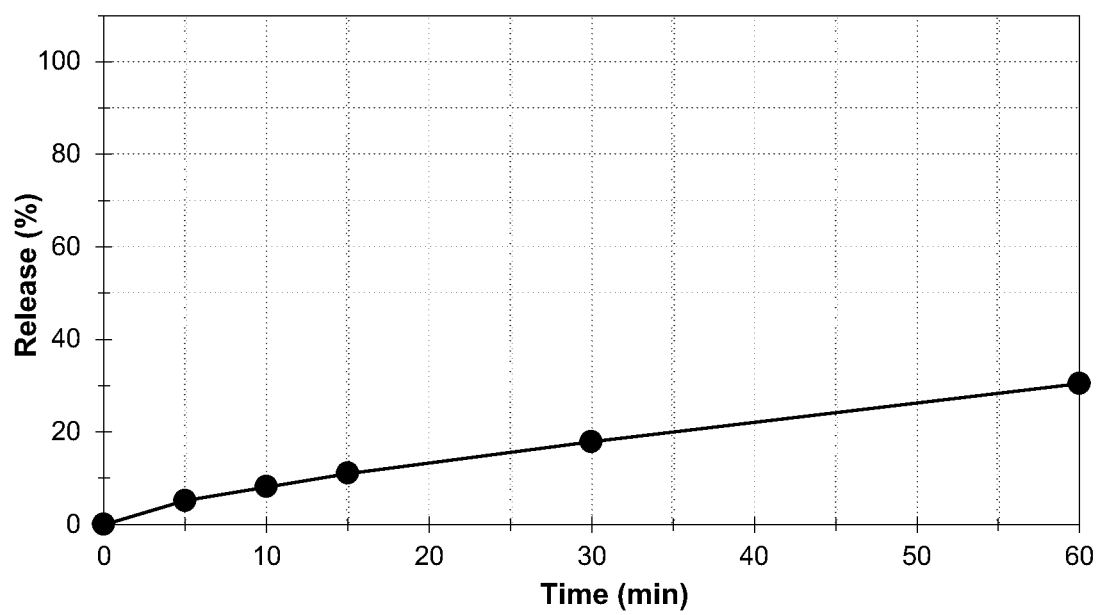
FIG. 13 illustrates the release profile of the diclofenac orally disintegrating tablets (ODTs) obtained in Example 7.

The cumulative release of the diclofenac ODTs is illustrated in FIG. 13. The actual release profile data is provided in the table below:

| % dissolved diclofenac | | |
| --- | --- | --- |
| Time (min) | Mean value | Standard deviation |
| 0 | 0.0 | 0.0 |
| 5 | 5.2 | 0.3 |
| 10 | 8.2 | 0.3 |
| 15 | 11.1 | 0.4 |
| 30 | 17.9 | 0.3 |
| 60 | 30.5 | 0.5 |

When granulated with Eudragit E PO, the cumulative diclofenac release in this phase after 60 minutes was about 30%. In the acidic phase, the excipient would dissolve. In that case the release of the active ingredient would occur in the subsequent buffer phase.

Example 8

Behavior of Diclofenac Under the Conditions Experienced after Oral Administration The following scheme shows the way of pharmaceutical formulation after oral administration:

Way after Oral Administration

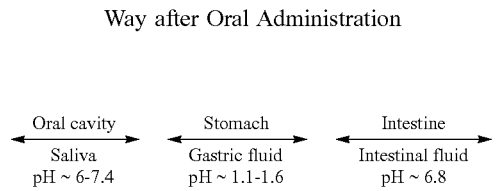

Solubility Studies

The solubility of diclofenac free acid, sodium and potassium was comparatively evaluated in media reflecting the oral way of administration, as e.g. with different pH values. The equilibrium solubility was determined using the saturation shake-flask method. Briefly, an excess amount of drug was added into the different media maintained at 37±0.5° C. and shaken for at least 24 hours. After equilibrium was reached, the excess of solid was removed and the diclofenac concentration in the supernatant solutions was determined by HPLC.

As expected, diclofenac shows a pH-dependent solubility. However, it is obvious that the free acid shows poorer solubility properties than the salts, as e.g. in the media tested.

The following table shows the solubility values of diclofenac free acid and its sodium and potassium salt in different media (mean±SD (n=3))

| | Solubility at 37° C. (μg/ml) - D/S (ml) | | |
| --- | --- | --- | --- |
| Solvent/media | Diclofenac acid | Diclofenac sodium | Diclofenac potassium |
| Water (purified) | 9.61 ± 0.10 | 89237 ± 0.15 | 94318 ± 0.08 |
| 0.1N HCl pH 1.1 | 2.49 ± 0.15 | 2.71 ± 0.06 | 2.40 ± 0.05 |
| Simulated gastric fluid pH 1.6 | 1.72 ± 0.01 | 1.63 ± 0.76 | 1.58 ± 0.82 |
| Simulated saliva pH 7.4 | 1005 ± 1.45 | 20349 ± 2.42 | 19431 ± 3.76 |
| Phosphate buffer pH 6.8 | 637 ± 0.05 | 1529 ± 0.06 | 1147 ± 0.06 |
| Simulated intestinal fluid pH 6.8 | 805 ± 0.01 | 13044 ± 0.76 | 13321 ± 0.82 |

Figure 14:
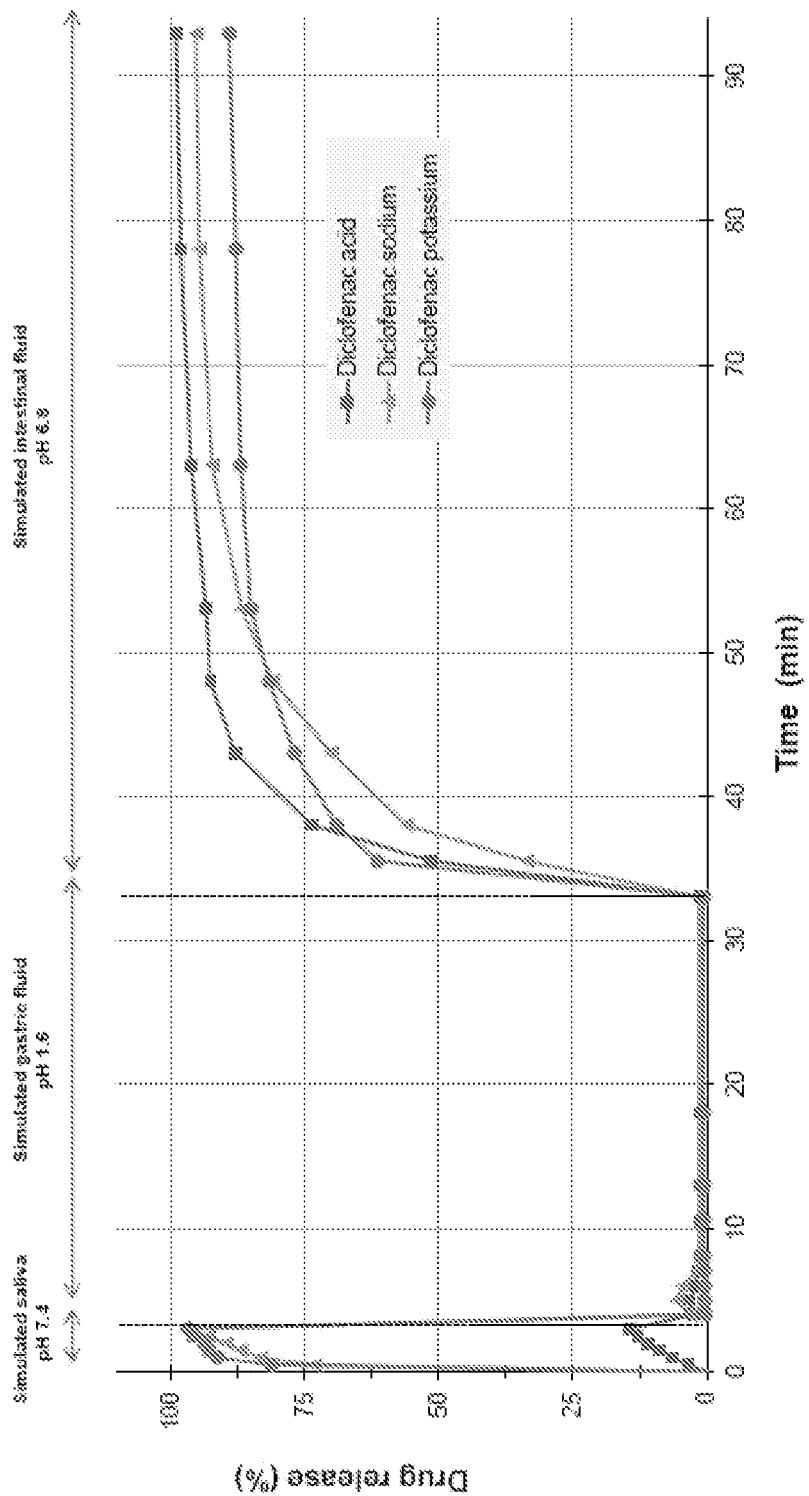
FIGS. 14 and 15 illustrate the comparison of the dissolution profiles from diclofenac free acid, sodium and potassium prototypes (ODTs) in phosphate buffer pH 6.8 after 2 h contact in 0.1 N HCl pH 1.1 obtained in Example 8.
Figure 15:
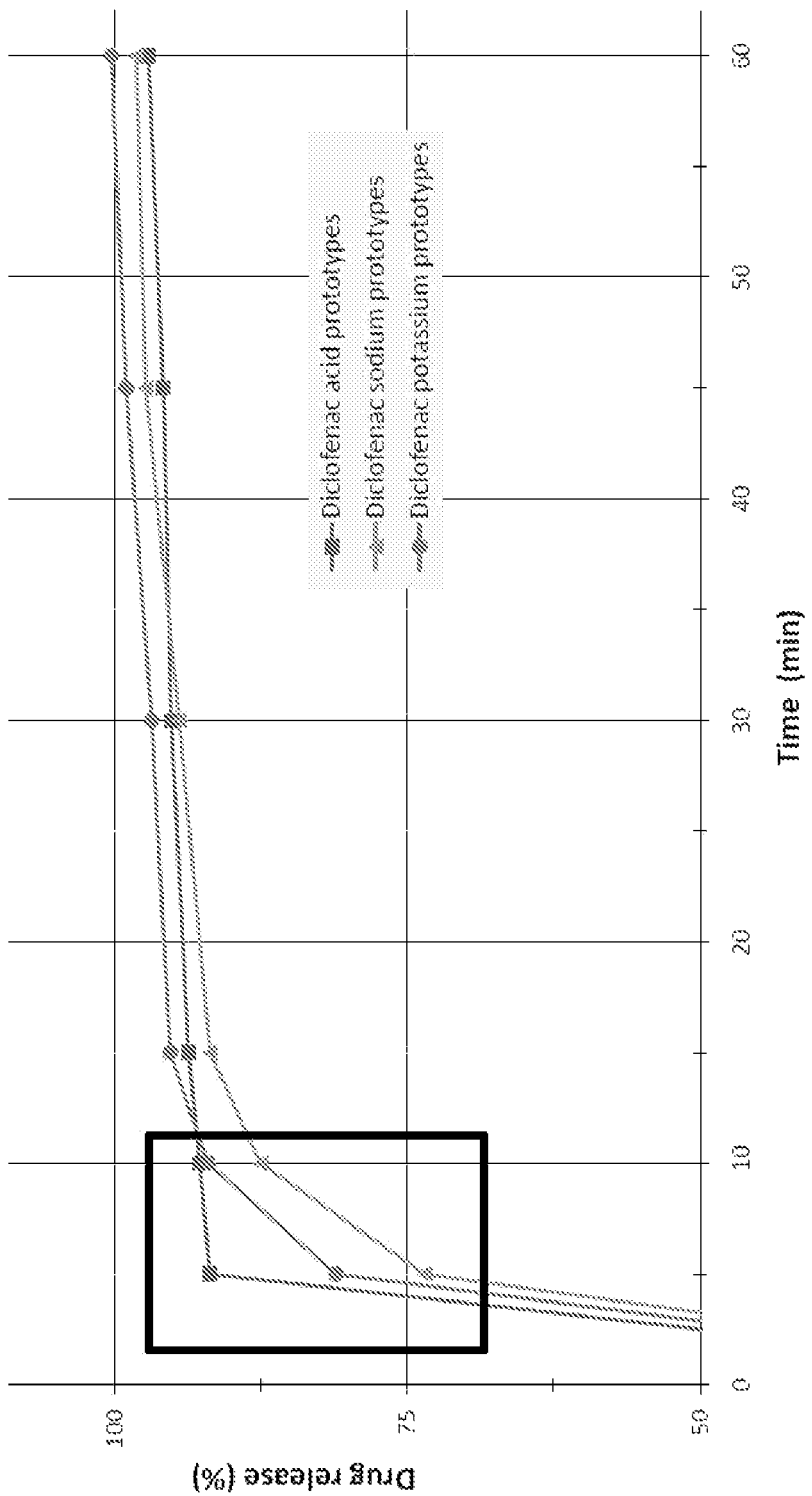

In FIGS. 14 and 15, the dissolution profiles of pharmaceutical compositions comprising diclofenac acid, sodium and potassium are shown under compendial pH-change conditions during the dissolution test. After being in contact with an acidic phase (2 hours), the dissolution of diclofenac salts is slower than that of diclofenac free acid.

The present data surprisingly demonstrate that the free acid exhibits improved release characteristics in the intestinal environment, the site of absorption, and in particular that these release characteristics could be fasted compared to the salts after. This effect is even more unexpected, since the solubility characteristics of the free acid are usually lower than those of the salts in most of the media and pH value as shown above. Thus, it was surprisingly found following the way of oral administration, diclofenac acid shows improved dissolution characteristics compared to the salts (FIGS. 14 and 15).

TABLE

Dissolution data from diclofenac free acid, sodium and potassium in phosphate buffer pH 6.8 after 2 h contact in 0.1N HCl pH 1.1; mean ± SD (n = 3) (FIG. 14 and 15)

| | Drug release (%) | | |
| --- | --- | --- | --- |
| Time points (min) | Diclofenac acid | Diclofenac sodium | Diclofenac potassium |
| 0 | 7.7 | 6.2 | 7.8 |
| 5 | 93.6 | 71.9 | 80.0 |
| 10 | 91.7 | 86.5 | 90.7 |
| 15 | 92.6 | 91.5 | 95.1 |
| 30 | 94.3 | 95.2 | 96.7 |
| 45 | 94.6 | 99.2 | 99.2 |
| 60 | 95.8 | 99.7 | 100.3 |

Example 9

Taste-Masking of Diclofenac Acid

To achieve suitable taste-masking of a bitter active pharmaceutical ingredient (API), such as diclofenac, it is commonly assumed that a polymer could be applied, i.e. by "surrounding" the particles with such a polymer. Such polymer application prevents the API particles to contact the surrounding environment, e.g. the saliva in the mouth. Therefore, the API particles are not released, cannot dissolve and thus are tasteless.

The amount of polymer used to taste-mask any API particles need to be in a sufficient amount in order to completely "surround/cover" the particles.

As already outlined above, the smaller the particles the faster are their dissolution characteristics. However, the smaller the particles the higher are their surface area and the more polymer need to be applied to sufficiently taste-mask the particles. A high amount of polymer, as already outlined above, also influence the bioavailability of the API drug, since the dissolution characteristics of the polymer rate-limits the disintegration of the pharmaceutical composition. Hence, a high surface area, not only complicates to sufficiently taste-mask the API particles but also influence the immediate-release characteristics of the pharmaceutical composition.

The amount of polymer for sufficiently taste-masking any bad tasting drug is typically 1 and 2 mg per $cm^2$ of drug particles. Thus, 1 mg of polymer used per $cm^2$ of drug particles is the recommended minimal amount to achieve a suitable taste-masking effect in order to provide a palatable pharmaceutical composition.

However, in the examples of the present invention, as e.g. the examples 1 and 2, diclofenac free acid was used in an average particle size of 7 μm. In more details, the theoretical ratio API/polymer of a pharmaceutical composition of diclofenac acid with this particle size and thus the corresponding surface area as recommended should be about 2/1.

Surprisingly, in examples 1 and 2 of the present invention, the ratio API/polymer is e.g. ~9/1 for example 1 and ~13.5/1 for example 2. Therefore, with the present invention, it is possible to reduce the amount of polymer in the pharmaceutical composition from about 80 to 90% for sufficient taste-masking characteristics.

Figure 16:
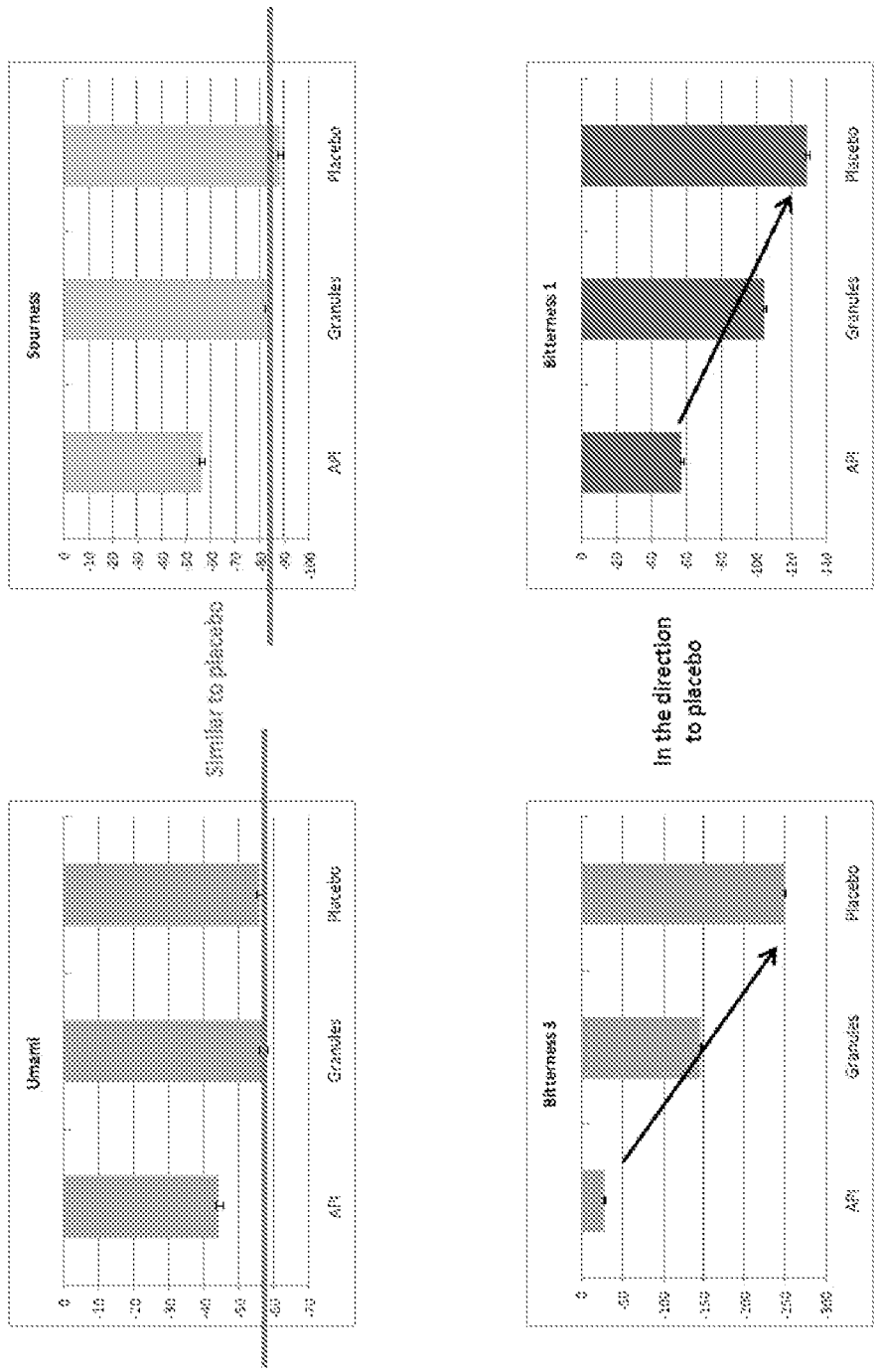
FIG. 16 illustrates the responses from selected sensors of an analytical taste sensing system of taste-masked diclofenac pharmaceutical composition (granule) compared to the pure diclofenac drug (API) and its corresponding drug-free formulation (placebo) obtained in Example 9 referring to Examples 1 and 2.

Indeed, a pharmaceutical composition as described in the present invention, i.e. with very low amounts of polymer compared to diclofenac, could achieve improved taste properties. In FIG. 16, responses from a taste sensing system to a pharmaceutical composition of the present invention are shown. In particular, responses from sensors detecting the taste sensations umami, sourness and bitterness (2 different sensors) are described. It is obviously shown that a granule composition as described in the present invention is detected differently than diclofenac. More particularly, the granule composition could be detected similarly to its corresponding drug-free formulation (umami and sourness sensors) which represents a good-tasting formulation. For the other sensors (bitterness), the response obtained is intermediate to that of diclofenac and the placebo meaning that a clear taste-masking effect is established.

The polymer as used in the present invention is not soluble at pH>5. Therefore, the polymer of the present invention does not dissolve in the mouth. Therefore, if the polymer surrounds the diclofenac particles, it protects diclofenac from contacting the saliva. Thus, it decreases/avoids the risks of diclofenac dissolution and taste perception at the site of administration, i.e. the mouth, and provides a taste-masking effect.

However, the polymer dissolves at pH<5, so in the stomach, after swallowing allowing diclofenac particles to be dispersed in the stomach. It has to be noticed that said particles do not dissolve in the stomach because of their poor solubility properties in this environment).

When diclofenac free acid particles finally enter the intestine, where they are soluble, they are directly dissolved at their site of absorption. This would last longer if they were not previously dispersed in the stomach.

In the examples of the present invention, it was surprisingly shown that the low amount of polymer comprised in the pharmaceutical compositions provide fast release rate in conditions closed to intestinal conditions while still providing enhanced taste masking properties.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A pharmaceutical composition comprising granules in which diclofenac, in a free acid form, and a (meth)acrylic polymer having at least one tertiary amino group are blended; wherein a ratio between the (meth)acrylic polymer and the diclofenac is from 1:20 to 1:8; and wherein said granules do not have a taste-masking coating and said (meth)acrylic polymer is present in the pharmaceutical composition in an amount ranging from 1.0 to 20.0 wt. % based on the total weight of the pharmaceutical composition.

2. The pharmaceutical composition according to claim 1; wherein the diclofenac has a particle size between 1 and 100 μm.

3. The pharmaceutical composition according to claim 1; wherein said (meth)acrylic polymer is poly(butyl methacrylate-co-(2-dimethylaminoethyl) methacrylate-co-methyl methacrylate).

4. The pharmaceutical composition according to claim 3; wherein the poly(butyl methacrylate-co-(2-dimethylaminoethyl) methacrylate-co-methyl methacrylate) has a ratio of butyl methacrylate to (2-dimethylaminoethyl) methacrylate to methyl methacrylate is in the range of 0.5-2:1-3:1.

5. The pharmaceutical composition according to claim 1; wherein said (meth)acrylic polymer has a weight average molar mass in the range of 40,000 to 54,000 g/mol.

6. The pharmaceutical composition according to claim 1; wherein said diclofenac is the only active ingredient in said pharmaceutical composition.

7. A tablet comprising:
the pharmaceutical composition according to claim 1.

8. The pharmaceutical composition according to claim 1; wherein the ratio between (meth)acrylic polymer and diclofenac is between 1:15 and 1:9.

9. The pharmaceutical composition according to claim 1; wherein a ratio between (meth)acrylic polymer and diclofenac is from 1:20 to 1:10.

* * * * *